United States Patent [19]
Boutillon et al.

[11] Patent Number: 6,015,564
[45] Date of Patent: *Jan. 18, 2000

[54] CYTOTOXIC T LYMPHOCYTE-INDUCING LIPOPEPTIDES AND USE AS VACCINES

[75] Inventors: Christophe Boutillon, Lille; Frederic Martinon, Montrouge; Christian Sergheraert, Morbecque; Remy Magne, L'Etang la Ville; Helene Gras-Masse, Merignies; Elisabeth Gomard, Paris; Andre Tartar, Vitry en Artois; Jean-Paul Levy, Paris, all of France

[73] Assignees: Institut Pasteur de Lille; Institut National de la Sante et de la Recherche Medicale (INSERM), both of France

[ * ] Notice: This patent is subject to a terminal disclaimer.

[21] Appl. No.: 09/248,082

[22] Filed: Feb. 10, 1999

Related U.S. Application Data

[63] Continuation of application No. 08/251,472, May 31, 1994, Pat. No. 5,871,746, which is a continuation-in-part of application No. 07/810,722, Dec. 18, 1991, abandoned.

[30] Foreign Application Priority Data

Dec. 18, 1990 [FR] France ..... 90 15870

[51] Int. Cl.$^7$ ..... A61K 39/21; A61K 39/00; A61K 39/12; C07K 1/00
[52] U.S. Cl. ..... 424/208.1; 530/350; 424/188.1; 424/184.1; 424/204.1
[58] Field of Search ..... 424/208.1, 188.1, 424/184.1, 204.1; 530/350

Primary Examiner—Jeffrey Stucker
Assistant Examiner—Hankyel T. Park
Attorney, Agent, or Firm—Bierman, Muserlian and Lucas

[57] ABSTRACT

Cytotoxic lymphocyte-inducing lipopeptides comprising a peptide part having between 10 and 40 amino acids approximately and comprising at least one antigenic determinant. The lipopeptides also comprise one or more chains derived from fatty acids and one or more modified steroid groups. Said lipopeptides may be used for immunizing the human or animal body against pathogenic agents such as viruses or parasites. The peptide part may, in particular, be a fragment of the protein encoded by the ENV gene, by the NEF gene or by the GAG gene of HIV viruses.

9 Claims, 6 Drawing Sheets

```
                        SEQUENCE LISTING (1) GENERAL INFORMATION:

(iii) NUMBER OF SEQUENCES:   11

(2) INFORMATION FOR SEQ ID NO:1:

(i) SEQUENCE CHARACTERISTICS:
        (A) LENGTH:   11
        (B) TYPE:   amino acid
        (C) STRANDEDNESS:   unknown
        (D) TOPOLOGY:   linear (ii) MOLECULE TYPE:   peptide (v) FRAGMENT TYPE:   internal (vi) ORIGINAL SOURCE:
        (A) ORGANISM: Influenza (ix) FEATURE:
        (B) LOCATION: NP 147-158

(xi) SEQUENCE DESCRIPTION: SEQ  ID NO:1:

Thr Tyr Gln Arg Thr Arg Ala Leu Val Thr Gly
1               5                   10

(2) INFORMATION FOR SEQ ID NO:2:

(i) SEQUENCE CHARACTERISTICS:
        (A) LENGTH:   16
        (B) TYPE:   amino acid
        (C) STRANDEDNESS:   unknown
        (D) TOPOLOGY:   linear (ii) MOLECULE TYPE:   peptide (v) FRAGMENT TYPE:   internal (vi) ORIGINAL SOURCE:
        (A) ORGANISM: HIV-1

(ix) FEATURE:
        (B) LOCATION: ENV 312-327

(xi) SEQUENCE DESCRIPTION: SEQ  ID NO:2:

Ile Arg Ile Gln Arg Gly Pro Gly Arg Ala Phe Val
1               5                   10

Thr Ile Gly Lys
15

(2) INFORMATION FOR SEQ ID NO:3:

(i) SEQUENCE CHARACTERISTICS:
```

```
            (A) LENGTH:  34
            (B) TYPE:  amino acid
            (C) STRANDEDNESS:  unknown
            (D) TOPOLOGY:  linear (ii) MOLECULE TYPE:  peptide (v) FRAGMENT TYPE:  internal (vi) ORIGINAL SOURCE:
            (A) ORGANISM:  HIV-1

(ix) FEATURE:
            (B) LOCATION:  ENV 302-335

(xi) SEQUENCE DESCRIPTION: SEQ  ID NO:3:

Thr Arg Pro Asn Asn Asn Thr Arg Lys Ser Ile Arg
 1               5                  10

Ile Gln Arg Gly Pro Gly Arg Ala Phe Val Thr Ile
        15                  20

Gly Lys Ile Gly Asn Met Arg Gln Ala His
25                  30

(2) INFORMATION FOR SEQ ID NO:4:

(i) SEQUENCE CHARACTERISTICS:
            (A) LENGTH:  26
            (B) TYPE:  amino acid
            (C) STRANDEDNESS:  unknown
            (D) TOPOLOGY:  linear (ii) MOLECULE TYPE:  peptide (v) FRAGMENT TYPE:  internal (vi) ORIGINAL SOURCE:
            (A) ORGANISM:  HIV-1

(ix) FEATURE:
            (B) LOCATION:  NEF 101-125

(xi) SEQUENCE DESCRIPTION: SEQ  ID NO:4:

Ser Val Arg Pro Lys Val Pro Leu Arg Ala Met Thr
 1               5                  10

Tyr Lys Leu Ala Ile Asp Met Ser His Phe Ile Lys
        15                  20

Glu Lys
25

(2) INFORMATION FOR SEQ ID NO:5:

(i) SEQUENCE CHARACTERISTICS:
            (A) LENGTH:  23
            (B) TYPE:  amino acid
            (C) STRANDEDNESS:  unknown
            (D) TOPOLOGY:  linear (ii) MOLECULE TYPE:  peptide (v) FRAGMENT TYPE:  internal (vi) ORIGINAL SOURCE:
            (A) ORGANISM:  HIV-1

(ix) FEATURE:
            (B) LOCATION:  NEF 125-147

(xi) SEQUENCE DESCRIPTION: SEQ  ID NO:5:

Glu Lys Gly Gly Leu Glu Gly Ile Tyr Tyr Ser Ala
 1               5                  10
```

```
Arg Arg His Arg Ile Leu Asp Met Tyr Leu Glu
        15                  20
```

(2) INFORMATION FOR SEQ ID NO:6:

(i) SEQUENCE CHARACTERISTICS:
        (A) LENGTH: 24
        (B) TYPE: amino acid
        (C) STRANDEDNESS: unknown
        (D) TOPOLOGY: linear (ii) MOLECULE TYPE: peptide (v) FRAGMENT TYPE: internal (vi) ORIGINAL SOURCE:
        (A) ORGANISM: HIV-1

(ix) FEATURE:
        (B) LOCATION: NEF 155-178

(xi) SEQUENCE DESCRIPTION: SEQ ID NO:6:

```
Asp Trp Gln Asp Tyr Thr Ser Gly Pro Gly Ile Arg
1               5                   10

Tyr Pro Lys Thr Phe Gly Trp Leu Trp Lys Leu Val
15                  20
```

(2) INFORMATION FOR SEQ ID NO:7:

(i) SEQUENCE CHARACTERISTICS:
        (A) LENGTH: 25
        (B) TYPE: amino acid
        (C) STRANDEDNESS: unknown
        (D) TOPOLOGY: linear (ii) MOLECULE TYPE: peptide (v) FRAGMENT TYPE: internal (vi) ORIGINAL SOURCE:
        (A) ORGANISM: HIV-1

(ix) FEATURE:
        (B) LOCATION: NEF 201-225

(xi) SEQUENCE DESCRIPTION: SEQ ID NO:7:

```
Ser Lys Trp Asp Asp Pro Trp Gly Glu Val Leu Ala
1               5                   10

Trp Lys Phe Asp Pro Thr Leu Ala Tyr Thr Tyr Glu
        15                  20

Ala
25
```

(2) INFORMATION FOR SEQ ID NO:8:

(i) SEQUENCE CHARACTERISTICS:
        (A) LENGTH: 27
        (B) TYPE: amino acid
        (C) STRANDEDNESS: unknown
        (D) TOPOLOGY: linear (ii) MOLECULE TYPE: peptide (v) FRAGMENT TYPE: internal (vi) ORIGINAL SOURCE:
        (A) ORGANISM: HIV-1

(ix) FEATURE:
        (B) LOCATION: NEF 221-247

(xi) SEQUENCE DESCRIPTION: SEQ ID NO:8:

```
Tyr Thr Tyr Glu Ala Tyr Ala Arg Tyr Pro Glu Glu
 1               5                  10

Leu Glu Ala Ser Gln Ala Cys Gln Arg Lys Arg Leu
            15              20

Glu Glu Gly
25
```

(2) INFORMATION FOR SEQ ID NO:9:

(i) SEQUENCE CHARACTERISTICS:
        (A) LENGTH: 31
        (B) TYPE: amino acid
        (C) STRANDEDNESS: unknown
        (D) TOPOLOGY: linear (ii) MOLECULE TYPE: peptide (v) FRAGMENT TYPE: internal (vi) ORIGINAL SOURCE:
        (A) ORGANISM: SIV (ix) FEATURE:
        (B) LOCATION: GAG 165-195

(xi) SEQUENCE DESCRIPTION: SEQ ID NO:9:

```
Lys Phe Gly Ala Glu Val Val Pro Gly Phe Gln Ala
 1               5                  10

Leu Ser Glu Gly Cys Thr Pro Tyr Asp Ile Asn Gln
            15              20

Met Leu Asn Cys Val Gly Asp
25                  30
```

(2) INFORMATION FOR SEQ ID NO:10:

(i) SEQUENCE CHARACTERISTICS:
        (A) LENGTH: 36
        (B) TYPE: amino acid
        (C) STRANDEDNESS: unknown
        (D) TOPOLOGY: linear (ii) MOLECULE TYPE: peptide (v) FRAGMENT TYPE: internal (vi) ORIGINAL SOURCE:
        (A) ORGANISM: SIV (ix) FEATURE:
        (B) LOCATION: GAG 246-281

(xi) SEQUENCE DESCRIPTION: SEQ ID NO:10:

```
Gln Ile Gln Trp Met Tyr Arg Gln Gln Asn Pro Ile
 1               5                  10

Pro Val Gly Asn Ile Tyr Arg Trp Ile Gln Leu Gly
            15              20

Leu Gln Lys Cys Val Arg Met Tyr Asn Pro Thr Asn
25                  30                  35
```

(2) INFORMATION FOR SEQ ID NO:11:

(i) SEQUENCE CHARACTERISTICS:
        (A) LENGTH: 11
        (B) TYPE: amino acid
        (C) STRANDEDNESS: unknown
        (D) TOPOLOGY: linear (ii) MOLECULE TYPE: peptide

```
    (v) FRAGMENT TYPE:  internal (vi) ORIGINAL SOURCE:
        (A) ORGANISM: HIV-1

(ix) FEATURE:
        (B) LOCATION: NEF 164-178

(xi) SEQUENCE DESCRIPTION: SEQ  ID NO:11:

Thr Ser Gly Pro Gly Ile Arg Tyr Pro Lys Thr
1               5                   10
```

CYTOTOXIC T LYMPHOCYTE-INDUCING LIPOPEPTIDES AND USE AS VACCINES

PRIOR APPLICATIONS

This application is a continuation of U.S. patent application Ser. No. 251,472 filed May 31, 1994, now U.S. Pat. No. 5,871,746 which is a continuation-in-part of U.S. patent application Ser. No. 810,722 filed Dec. 18, 1991, now abandoned.

FIELD OF THE INVENTION

The subject of the present invention is novel cytotoxic T lymphocyte-inducing lipopeptides.

The subject is furthermore the use of such lipopeptides as vaccines.

DESCRIPTION OF THE PRIOR ART

Most vaccines used induce a response through antibodies. However, it has been shown that cytotoxic lymphocytes can effectively protect mice against various pathogenic microorganisms (Skehel et al., Proc. Natl. Acad. Sci. USA. 1982, 79; 968; Lukacher et al., Exp. Med. 1984, 160: 814). This has also been shown for human cytotoxic T lymphocytes raised against cytomegaloviruses (Quinnan et al., N. Engl. J. Med. 1982, 307: 7; Rook et al., Am. J. Med. 1984, 76: 385). However, little is known about inducing immunity due to lymphocytes.

Some authors have tried to induce cytotoxic T lymphocytes (CTL) in vivo using peptides derived from ovalbumin (Carbone et al. J. Exp. Med. 169: 603, Ishioka et al. 1989, J. Immunol. 143: 1094). These authors obtained immunizations, but these results are specific for peptides derived from ovalbumin.

AICHELE et al. ((1990) J. Exp. Med. 171: 1815) succeeded, for their part, in inducing a cytolytic T response by repeated injections in vivo of a synthetic peptide in emulsion in incomplete Freund's adjuvant. These authors do not indicate the importance of the adjuvant under their immunization conditions. However, they suggest that an adjuvant is necessary for obtaining such a response.

The application EP-203,676 relates to a vaccine intended to induce a T cell mediated response comprising some peptide-fatty acid conjugates. The fatty acid which is used is the palmitic acid. However, this vaccine comprises also Freund's adjuvant.

To the knowledge of the applicant, only DERES et al. (Nature, Volume 342, Nov. 30, 1989) have described the use of a synthetic lipopeptide to induce cytotoxic T lymphocytes (CTL) in vivo. In this article, the NP 147–158 fragment of a nucleoprotein of the influenza virus is coupled to tripalmitoyl-S-glyceryl-cysteinylserylserine (P3CSS). It is shown that the NP 147–158 peptide-P3CSS lipid conjugate induces a CTL response against target cells infected by the influenza virus, whereas mice immunized with the NP 147–158 peptide alone or with the Ser Ser-NP 147–158 peptide do not generate cytotoxic T lymphocytes against this virus.

It should also be noted that lipopeptides have already been used to induce immunological reactions to specific antigens, but the responses generated implied the synthesis of antibodies and not T lymphocyte responses. HOPP (Molecular Immunology, 21, 13–16, 1984) has shown that antibodies raised against a determinant of the hepatitis B virus could be obtained by immunizing rabbits using a molecule consisting of a peptide of 15 amino acids corresponding to the antigenic determinant of the hepatitis B virus and of a pseudolipide residue, dipalmitoyl lysine.

The application EP-93 851 describes some lipopeptides comprising a peptidic sequence of 6 to 15 aminoacids bound to a lipophylic part. This lipophylic part can be a fatty acid such as palmitic, stearic, behenic, oleic or mycolic acids. It is mentioned that these lipopeptides induce the antibodies synthesis.

The publication of Wiesmüller et al. (Vaccine, volume 7, n° 1, 29–33, 1989) describes the use of a lipopeptide comprising a part of the sequence of the virus FDMV ($VP_1$) and the lipid $P_3CSS$ to induce the synthesis of antibodies.

The abstract of the publication of Jacob et al. (Chemical Abstracts, vol. 104, n° 21, 472, abstract 184.455 x, 1986) relates to the induction of the antibodies synthesis by a lipopeptide comprising the tetanus toxine bound to a dipalmitoyl rest.

The abstract of the publication of Watari et al. (Chemical Abstracts, vol. 106, p 516, abstract n° 154 381 u, 1987) relates to the use of some peptides corresponding to the N-terminal region of the glycoprotein D of the virus HSV coupled to the palmitic acid. It is clearly indicated that there is induction of a T cells mediated response but that this response is not due to cytotoxic T lymphocytes.

Two other references relate to the synthesis and the structural study of lipopeptides.

The International Application WO 89 10348 relates to some fatty acids derivated lipopeptides, such as the aminoeicosanic, aminodecanoic, aminotetradecanoic, bromodecanoid and bromododecanoic acids.

It is mentioned that these compounds can be used as adjuvants and as carriers for vaccines, but without providing any mean to use these compounds.

The abstract of the publication of Mercy et al. (Chemical Abstracts, vol. 106, n° 25, 264, abstract n° 209,643 p, 1987) concerns the structural analysis of a lipopeptide composed of a fragment of the virus G protein and of a lysine-palmitoyl rest.

Besides, the U.S. application Ser. No. 628,596 relates to polypeptidic structures comprising an amino sequence taken in two regions of the NEF proteins corresponding to residues 73–94 and 113–147. However, the structure of the lipidic moiety is not disclosed and the application does not include any results concerning the use of such lipopeptides.

This analysis of the state of the art therefore shows that no technology applicable to various types of antigenic determinants has been developed which enables the induction of cytotoxic T lymphocytes to be obtained, with a high induced response, and which does not require the administration of an adjuvant.

GENERAL DESCRIPTION OF THE INVENTION

The applicant has shown, surprisingly, that a response of cytotoxic T lymphocytes against an antigen could be induced in a host organism by immunizing said organism with a lipopeptide complex containing one of the determinants of this antigen.

Even more surprisingly, the applicant has shown that this induction could be obtained for a large number of antigenic determinants of various pathogenic agents.

The subject of the present invention is therefore a lipopeptide comprising a peptide part having between 10 and 40 and preferably between 10 and 20 amino acids approximately and comprising at least one antigenic determinant, said lipopeptide also comprising one or more chains derived from fatty acids comprising between 10 and 20 carbon atoms and/or one or more steroid groups modified and coupled on the α-NH$_2$ or ε-NH$_2$ functional groups of said amino acids.

Said fatty acid derivatives may be in particular hexadecanoic acid, 2-aminohexadecanoic acid (D,L) of the following formula (I):

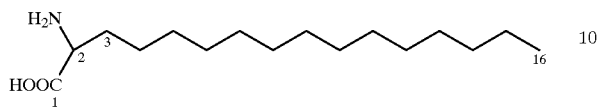

N-ε-palmitoyllysine (L) of the following formula (II):

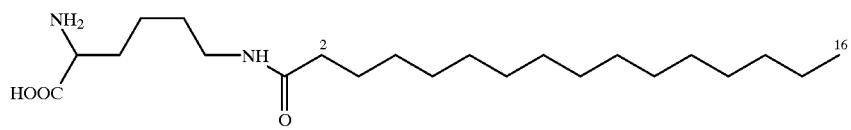

or its derivate having the following formula:

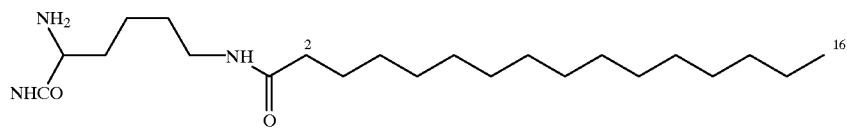

N,N'-dipalmitoyllysine (L) of the following formula (III):

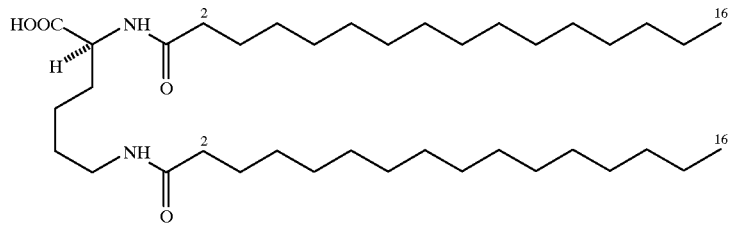

pimelautide of the following formula (IV):

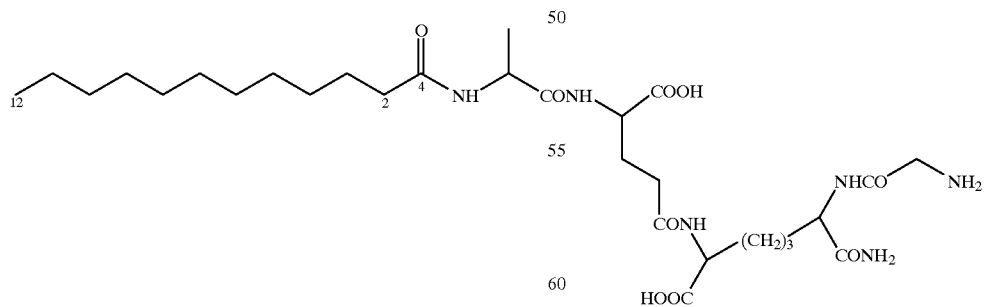

trimexautide of the following formula (V):

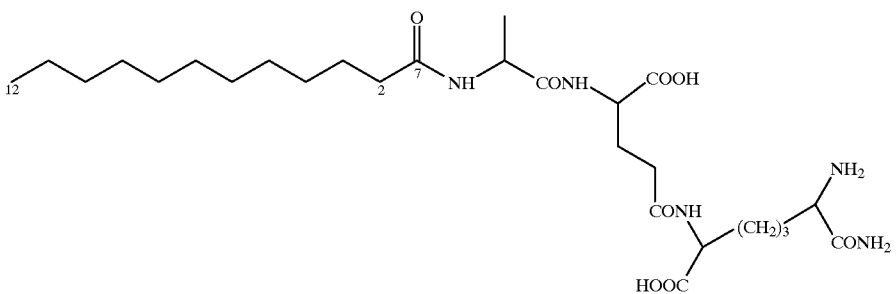

or one of their derivatives.

Said steroid groups may be N-ε-[(cholest-5-enyl-3-oxy)acetyl]lysine (L) of the following formula (VI):

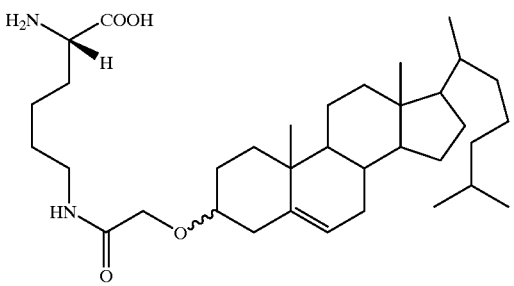

(cholest-5-enyl-3-oxy)acetic acid of the following formula (VII)

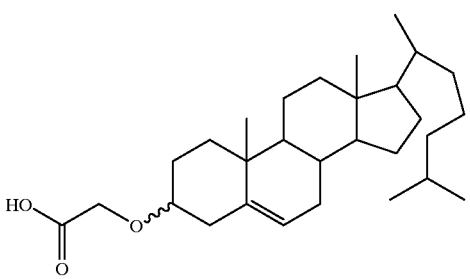

or one of their derivatives.

The peptide part may be a fragment of any protein derived from a pathogenic agent possessing an antigenic determinant.

Such proteins may be especially the proteins of the HIV1 or HIV2 virus, in particular the protein encoded by the ENV gene. In this case, the fragments 312–327, 302–336 or 307–331 may be advantageously used depending on the $HIV_1$-BRU sequence (Hyers, C. A. B. Rabson, S. F. Josephs, T. F. Smith and E. Wong-Staal (Eds.), 1989, Human retrovirus and AIDS, Los Alamos Laboratory II:59) of this protein, to form the conjugated lipopeptide molecule.

Such fragments of HIV proteins may be also the 66–97, 117–147 or 182–205 fragments of the protein encoded by the NEF gene or the 183–214 or 253–284 fragments of the protein encoded by the GAG gene.

The present invention relates moreover to pharmaceutical compositions containing an efficient quantity of at least one of the compounds above described in association with one or few diluents or adjuvants compatible and pharmaceutically acceptable.

These compositions are in particular intended for treating the diseases related with the HIV virus by induction of cytotoxic T lymphocytes.

The subject of the present invention is furthermore vaccines against viruses or parasites containing one of the above-described lipopeptides, and in particular vaccines against diseases linked to HIV viruses, said vaccines advantageously containing at least a fragment of a protein which is the product of the ENV gene, of the NEF gene or the GAG gene.

In particular, such a vaccine could contain the following fragments:
- 307–331 fragment of the protein encoded by the ENV gene,
- 66–97, 117–147 and 182–205 fragments of the protein encoded by the NEF gene, and
- 183–214 and 253–284 fragments of the protein encoded by the GAG gene.

The subject of the present invention is furthermore the use of the above-described lipopeptides for immunizing the human or animal body against pathogenic agents by inducing cytotoxic T lymphocytes. Such pathogenic agents may be viruses which have a substantial cytotoxic activity, in particular the HIV1 and HIV2 viruses, and certain parasites.

Said lipopeptides mays also be used against certain cancers in order to induce a CTL response specific for certain tumor cells.

The lipopeptides which are the subject of the present invention may be obtained from protein and pseudolipid constituents by methods known to a person skilled in the art, in particular, either by coupling the amino acids comprising the peptide part to the pseudolipid immobilized on a resin, that is to say by solid phase synthesis, or by coupling the pseudolipid to a peptide immobilized in a solid phase.

It should be noted that the lipopeptides according to the invention possess the notable advantage of being capable of being adapted for inducing cytotoxic T lymphocytes against any type of antigenic determinant of any pathogenic agent.

Additionally, the present invention also relates to the following synthetic intermediates:

2-tert-butyloxycarbonylaminohexadecanoic acid (D,L) of the following formula (VIII):

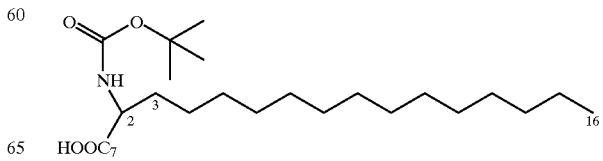

N-α-terbutyloxycarbonyl ε-palmitoyl-lysine (L) of the following formula (IX):
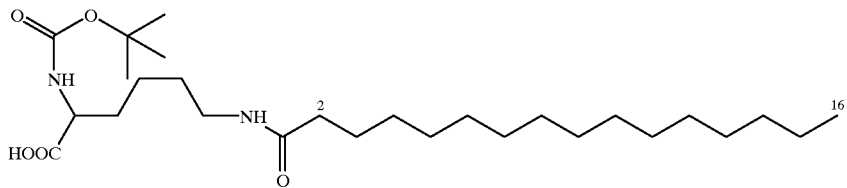
N-α-fluorenylmethyloxycarbonyl ε-palmitoyl-lysine (L) of the following formula (X):
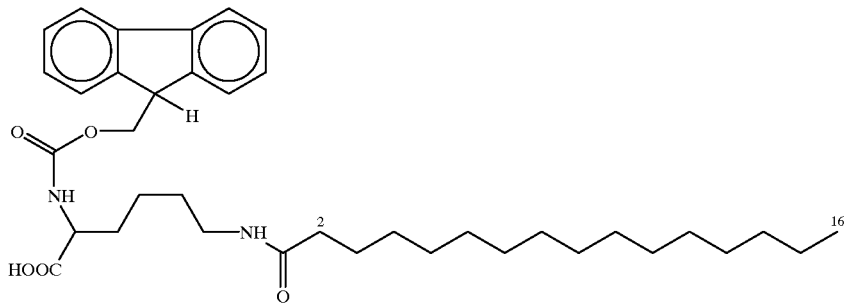
N-α-tert-butyloxycarbonyl ε-[(cholest-5-enyl-3-oxy)-acetyl]-lysine (L) of the following formula (XI):
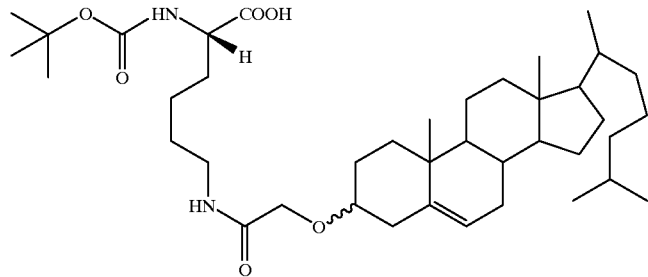
or N-α-fluorenylmethyloxycarbonyl ε-[(cholest-5-enyl-3-oxy)-acetyl]-lysine (L) of the following formula (XII):

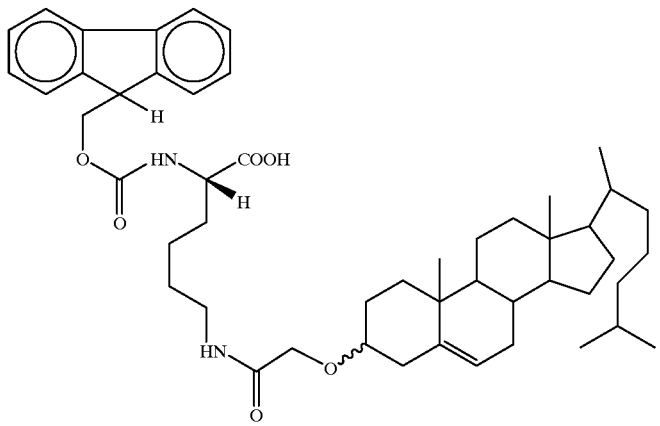

or one of their derivatives.

BRIEF DESCRIPTION OF THE DRAWINGS

The present invention is illustrated, without being limited in any manner, by the following examples of application in which.

Figure 1:
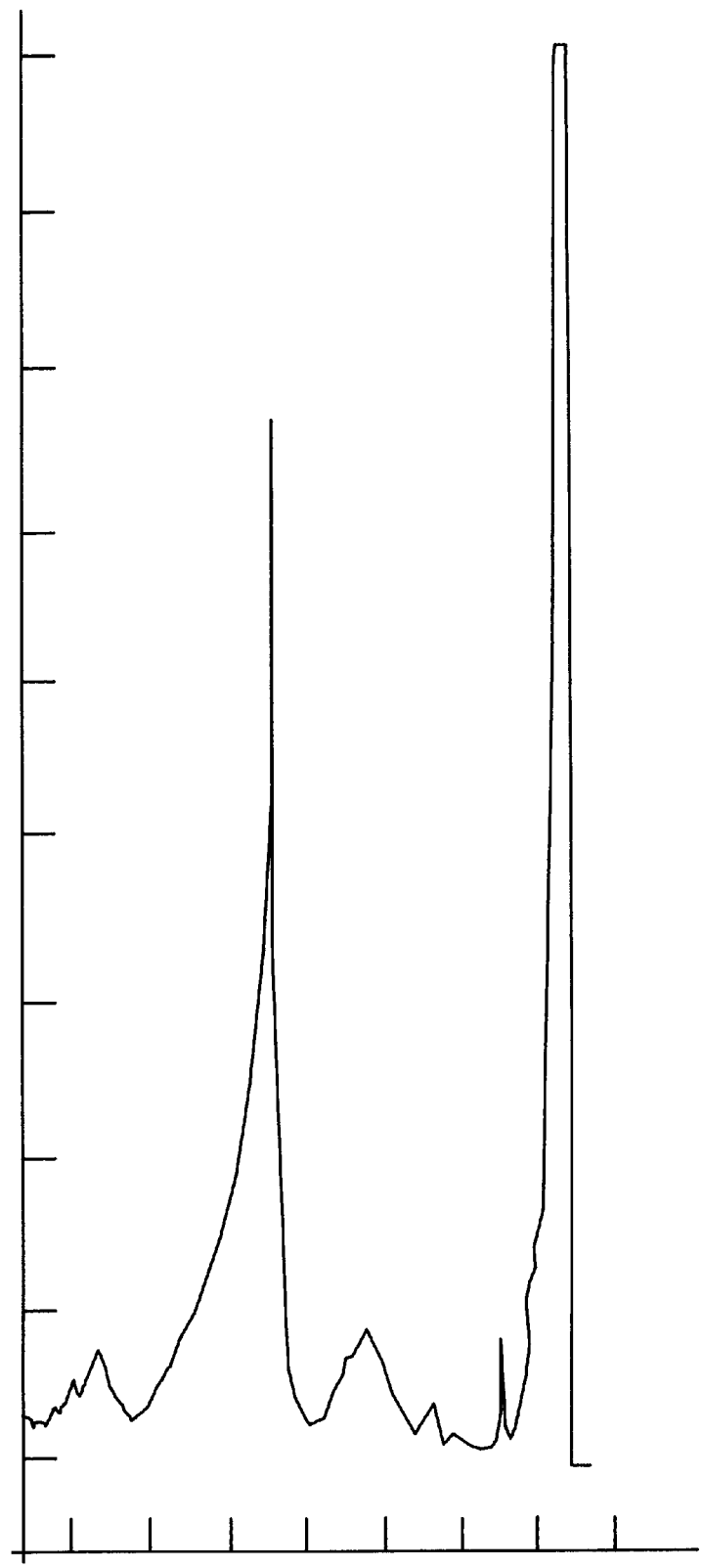
FIGS. 1 and 3 represent the reverse-phase HPLC spectra of the lipopeptide V3GP120, 312–327 succinyl during preparative and analytical electrophoreses respectively.

EXAMPLE 1
Synthesis of Pseudolipid Residues (or Hydrophobic Molecules)

1. Synthesis of 2-tert-butyloxycarbonyl-aminohexadecanoic acid.

1.1 Synthesis of 2-aminohexadecanoic acid.

Empirical formula: $C_{16}H_{33}NO_2$

Molecular mass: 271.44

Procedure:

0.0298 mole of 2-bromohexadecanoic acid (10 g) and 100 ml of a 28% solution of $NH_4OH$ are introduced into an autoclave previously cleaned with 50% nitric acid and 10% phosphoric acid. After stirring, the auto-clave is heated at 60° C. for 15 hours. The nascent amino derivative precipitates in the reaction medium. After cooling, the autoclave is washed, the water dispersed and the ethanol removed. The reaction mixture is filtered on sintered glass with a porosity of 4 The difference in solubility of the various products in ethanol medium enables the removal of traces of 2-bromohexadecanoic acid by rinsing.

Amount of precipitate obtained: 4.37 g; yield of 54%.

Remark: The insolubility of the amino derivative was checked in numerous solvents (water, ethanol, acetic acid at low temperature, 70% formic acid, ethyl acetate, toluene, toluene/acetonitrile, ethyl acetate/acetonitrile). Among all the solubilization assays tested, only the action of a specific detergent (tri-methylbenzylammonium hydroxide) or boiling acetic acid dissolved the amino derivative.

The dried precipitate is taken up in 150 ml of acetic acid which is refluxed until a yellowish clear solution is obtained. The colored pigments are absorbed on vegetable charcoal. After filtering on folded filter paper, the purified amino derivative is obtained by crystallization from the eluate. The white crystals obtained are recovered on sintered glass with a porosity of 4, washed with cold acetic acid before being dried in a desiccator over $P_2O_5$.

Yield: 46% (the product being in acetate form, a MW of 330.48 is used).

The purification yield is equal to 85%.

1.2. Synthesis of 2-tert-butyloxycarbonyl-aminohexadecanoic acid.

Empirical formula: $C_{21}H_{41}NO_4$

Molecular mass: 371.557.

Procedure:

Dissolution of 2-aminohexadecanoic acid.

1.1 equivalents of "Triton" (benzyltrimethyl-ammonium hydroxide) in solution at 40% in methanol (2.9 ml) as well as 100 ml of DMF are added to 5 mmol of amino acid in acetate form (1.655 g). The reaction mixture is left stirred at room temperature until complete dissolution. The DMF is then evaporated using a vane pump. The residue is dried in a desiccator over $P_2O_5$.

Protection of the amine functional group.

The dry residue is dissolved in a mixture consisting of 36 ml of water, 8 ml of 1N $KHCO_3$ and 30 ml of tert-butyl alcohol. 2.5 equivalents of terbutyl-dicarbonate (MW= 218.25) are added to this solution. The pH is adjusted to between 8 and 9 using a 1N solution of $Na_2CO_3$ and maintained constant during the initial hours of the reaction. The kinetics of coupling are monitored by thin-layer chromatography on silica.

After evaporating the tert-butyl alcohol under vacuum, the product is taken up in 100 ml of water. The aqueous phase is acidified to pH 3 with a 1N solution of HCl. The Boc-amino acid is extracted with ethyl acetate (2×100 ml). The organic phase is washed with distilled water, dried over anhydrous $Na_2SO_4$, filtered and then concentrated using a rotating evaporator. 4 ml of hexane are added to the oily residue. Crystallization of the Boc-amino acid is enhanced by cooling in a cold chamber. The white crystals are recovered on sintered glass with a porosity of 4, washed with hexane and dried in a desiccator over $P_2O_5$.

Yield: 16 to 18%.

1.3. Purification and Characterization

1.3.1. Purification

Successive recrystallizations made it possible to increase the purity (increase in the melting point). The purification led to a reduction in yield of not more than 2% for aminohexadecanoic acid and of not more than 1% for the protected amino acid.

1.3.2. Characterization

A. Melting Point

| Product | Melting point obtained |
| --- | --- |
| 2-Bromohexadecanoic acid | 56° C. |
| 2-Aminohexadecanoic acid | 144° C. |
| 2-tert-Butyloxycarbonyl-aminohexadecanoic acid | 85° C. |

B. Thin-layer Chromatography on Silica

The solutions (10 to 20 µl of a solution at 1 mg/ml) are deposited on thin-layer silica (Merck silica gel 60 without fluorescence indicator).

2-Bromohexadecanoic acid is dissolved in ethanol, 2-aminohexadecanoic acid in boiling acetic acid, and tert-butyloxycarbonyl-2-aminohexadecanoate in dichloromethane.

Choice of the migration solvent.

The various systems chosen are:

System A: butanol/ethyl acetate/acetic acid/water in the volume/volume proportions: 1/1/1/1.

System B: ethyl acetate/pyridine/acetic acid/water in the v/v proportions: 5/5/1/3.

System C: chloroform/methanol/acetic acid in the v/v proportions: 10/1/0.1.

Developing.

After migration in the system of suitable solvents, the thin layers are dried for 15 minutes at 120° C. before being developed after spraying with a developing reagent.

The ninhydrin reagent which is specific for primary amino functional groups enables the detection of the unprotected aminohexadecanoic acid but also of the Boc-amino acid, the spraying of 20% acetic acid followed by drying at 120° C. enabling the displacement of the Boc group.

The spraying using a reagent comprising 20 g of $(NH_4)_2SO_4$, 3 ml of $H_2SO_4$ and 100 ml of $H_2O$ enable the simultaneous developing of the three products. In this technique, the drying, after spraying, in the thin-layer chromatography is carried out using an epi-radiator (porcelain resistance with infrared radiation).

Result:

| Product | Solvents | Rf |
| --- | --- | --- |
| 2-Bromohexadecanoic acid | System A | 0.5 |
| | System B | 1 |
| | System C | 1 |
| 2-Aminohexadecanoic acid | System A | 0.82 |
| | System B | 0.94 |
| | System C | 0 |
| 2-tert-Butyloxycarbonyl-amino-hexadecanoic acid | System A | 1 |
| | System B | 1 |
| | System C | 0.67 |

| MM (g) | $(M-H)^-$ | Fragments: |
| --- | --- | --- |
| Theoretical MM | 370.557 | |
| Experimental MM | 370.8 | 270 |

The experimental molecular ion and the theoretical molecular ion have an identical mass. The molecular ion is fragmented; the Boc group (peak at 270) is released. The 296.6 peak represents the ion with a mass of 270 containing the CN group (nitro-cellulose).

2. Synthesis of $^3\beta$-(2'-carboxymethoxy)-cholest-5-ene.

2.1. Synthesis of cholesteryl tosylate.

Empirical formula: $C_{34}H_{53}SO_3$,

Molecular mass: 540.83,

Procedure:

After dissolving 25.86 mmol of cholesterol (10 g) in a minimum of pyridine (5 to 10 ml), an excess of tosyl chloride (10 g, 52.6 mmol) is added. After stirring for 12 hours, the pyridine is removed by evaporating to dryness. The residue is solubilized in 20 ml of acetone at high temperature (the temperature is maintained below 55° C. to avoid the formation of oil). The mixture is filtered. The cholesterol tosylate is obtained by crystallization from the eluate. The white crystals obtained are washed with cold acetone and dried in a desiccator over $P_2O_5$.

Yield: 82 to 85%.

2.2 Synthesis of $^3\beta$-(2'-hydroxyethoxy)-cholest-5-ene.

Empirical formula: $C_{29}H_{50}O_2$.

Molecular mass: 430.71.

Procedure:

30 ml of ethylene glycol (480 mmol) are added to 17.5 mmol of cholesteryl tosylate (10 g) dissolved in 120 ml of dioxane. The reaction mixture is refluxed for 4 hours at 120° C. After cooling, it is taken up in 150 ml of distilled water. The alcohol derivative formed is extracted with diethyl ether (3×200 ml). The ethereal phase is successively washed with 5% $NaHCO_3$ (2 200 ml) and distilled water (2×200 ml). After drying over anhydrous $Na_2SO_4$, the ethereal solution is concentrated until an oil is obtained. After adding 4 ml of hexane, the crystallization is started by rubbing and cooling in a cold chamber (4° C.). The white crystals are recovered on sintered glass with a porosity of 4 and washed with hexane before being dried in a desiccator over $P_2O_5$.

Yield: 32 to 34%.

2.3. Synthesis of $^3\beta$-(2'-carboxymethoxy)-cholest-5-ene.

Empirical formula: $C_{29}H_{48}O_3$,

Molecular mass: 444.69.

Procedure:

The oxidizing solution is prepared beforehand: it comprises 2.67 g of chromic anhydride, 2.3 ml of concentrated $H_2SO_4$, the volume being brought to 10 ml with distilled water. The oxidizing medium is added dropwise to 4.66 mmol (2 g) of $^3\beta$-(2'-hydroxyethoxy)-cholest-5-ene dissolved in 50 ml of acetone. The progress of the reaction is monitored by thin-layer chromatography. Once the reaction is completed, the reaction medium is taken up in 250 ml of distilled water. The acid derivative is extracted with ethyl acetate (3×200 ml). The organic phase is washed with distilled water (2×200 ml), dried over anhydrous Na$_2$SO$_4$ and concentrated until an oil is obtained. 4 ml of petroleum ether are added. The crystallization of the acid derivative is enhanced by cooling in a cold chamber (4° C.). The white crystals are recovered on sintered glass with a porosity of 4, washed with petroleum ether and dried in a desiccator over P$_2$O$_5$.

Yield: 29 to 31%.

2.4. Purification and Characterization

2.4.1. Purification

Cholesteryl p-toluenesulfonate is purified by successive recrystallizations in acetone. β-(2'-Hydroxyethoxy)cholest-5-ene and the acid derivative have both been purified by thick-layer chromatography on silica.

A. Thick-layer Chromatography on Silica

The depositions are carried out on a thick layer of silica (Merck silica gel 60 PF$_{254}$ with a fluorescence indicator), the spots being detected by ultraviolet radiation.

A solution containing 0.250 mg of product is deposited on the silica plate, the products have both been dissolved in dichloromethane.

| Product | Solvent | R$_f$ |
| --- | --- | --- |
| 3 β-(2'-Hydroxyethoxy)-cholest-5-ene | Petroleum ether/ethyl ether Volume/volume proportions: 1/1 | 0.48 |
| 3 β-(2'-Carboxymethoxy)-cholest-5-ene | Petroleum ether/ethyl ether/methanol v/v proportions: 10/10/3 | 0.52 |

The two products were extracted from the silica with methanol. A loss equivalent to about 30% of the amount deposited is observed for each of the products.

2.4.2. Characterization

A. Melting Point

| Product | Melting point (literature) | Melting point |
| --- | --- | --- |
| Cholesteryl para-toluene-sulfonate | 131.5° C.–132.5° C. | 128° C. |
| 3 β-(2'-Hydroxyethoxy) | 102° C.–104° C. | 99° C. |
| 3 β-(2'-Carboxymethoxy)-cholest-5-ene | 160° C.–161° C. | 157° C. |

B. Thin-layer Chromatography

The depositions (10 to 20 μl) of a 1 mg/ml solution are carried out on a thin layer of silica with a fluorescence indicator (Merck Kieselgel 60F$_{254}$).

The dissolution of the various products is carried out in dichloromethane.

After migration in the suitable solvent system, the thin layers are dried in air before being developed either by ultraviolet radiation or after spraying with HClO$_4$ (20%) and drying in an oven (120° C. for 20 minutes).

Result:

Various solvent systems.

System A: Ethyl ether/petroleum ether in the volume/volume proportions: 1/1.

System B: Ethyl ether/petroleum ether in the v/v proportions: 1/2.

System C: Petroleum ether/ethyl ether/methanol in the v/v proportions: 5/5/1.

System D: Petroleum ether/ethyl ether/methanol in the v/v proportions: 10/10/3.

System E: Petroleum ether/ethyl ether/methanol in the v/v proportions: 5/5/2.

System F: Ethyl ether.

| Product | Solvent system | R$_f$ |
| --- | --- | --- |
| Cholesterol | System A | 0.54 |
|  | System B | 0.3 |
|  | System F | 0.95 |
| Cholesteryl para-toluenesulfonate | System A | 0.85 |
|  | System B | 0.62 |
|  | System F | 1 |
| 3 β-(2'-Hydroxyethoxy)-cholest-5-ene | System A | 0.41 |
|  | System B | 0.24 |
|  | System F | 0.9 |
| 3 β-(2'-Carboxymethoxy)-cholest-5-ene | System A | 0 |
|  | System B | 0 |
|  | System C | 0.1 |
|  | System D | 0.42 |
|  | System E | 0.78 |
|  | System F effect: | Streaking R$_f$ 0 0.5 |

C. Mass Spectrometry (PDMS)

Analysis of the 3-β(2'-carboxymethoxy)cholest-5-ene.

| MM (g) | (M-H)$_-$ |
| --- | --- |
| Theoretical MM | 443.69 |
| Experimental MM | 443.1 |

The experimental molecular ion and the theoretical molecular ion have an identical mass.

D. $^{13}$C Nuclear Magnetic Resonance

Analysis of the 3-β(2'-carboxymethoxy)cholest-5-ene spectrum was carried out by comparison with the $^{13}$C NMR spectrum of cholesterol.

The dissolution of the cholesterol and the 3-β(2'-carboxymethoxy)cholest-5-ene was performed in deuterated chloroform.

Cholesterol spectrum.

| Peaks | d(ppm) obtained | attribution | theoretical d(ppm) |
| --- | --- | --- | --- |
| 1 | 140.7606 | C5 or C6 | alkene functional group: d(ppm) from 100 to 145 |
| 2 | 121.7064 | C5 or C6 |  |
| 3 | 78.5715 | CDCl$_3$ |  |
| 4 | 76.9981 | CDCl$_3$ |  |
| 5 | 75.4010 | CDCl$_3$ |  |
| 1' to 22' | 71 to 11 |  | alkane functional groups. |

$3\beta$-(2'-Carboxymethoxy)cholest-5-ene spectrum.

| Peaks | d(ppm) obtained | attribution | theoretical d(ppm) |
|---|---|---|---|
| 1 | 172.2923 | C5 or C6 | acid functional group: d(ppm) from 160 to 185 |
| 2 | 139.8394 | C5 or C6 | alkene functional group: d(ppm) from 100 to 145 |
| 3 | 122.5233 | C5 or C6 | alkene functional group |
| 4 | 80.5745 | C1' | ether functional group: d(ppm) from 45 to 80 |
| 5 | 79.2943 | C1' | + slight displacement |
|   | 78.5903 | CDCl$_3$ | |
| 7 | 77.0089 | CDCl$_3$ | |
| 8 | 75.4146 | CDCl$_3$ | |
| 9 to 31 | 65 to 11 | | alkane functional groups. |

E. Elemental Analysis

Elemental analysis of $_3\beta$-(2'-carboxymethoxy)cholest-5-ene gave the following results:

|  | Theoretical | Obtained |
|---|---|---|
| % carbon | 78.3 | 76.25 |
| % hydrogen | 10.9 | 10.9 |
| % oxygen | 10.8 | 12.5 |

EXAMPLE 2
Synthesis of the Lipopeptides

I. Method for coupling 2-aminohexadecanoic acid

The 312–327 region of gp120 of the HIV-1 LAV$_{BRU}$ virus (SEQ ID No:2) was chosen for sequences constructed in lipopeptide form in order to study the cytotoxic T response. 3 preparations were carried out using this sequence.

The synthesis was carried out in solid phase (MERRIFIELD R. B., 1963, J. Am. Chem. Soc. 85, 2149–2210).

All the lipopeptides were synthesized on a benzhydrylamine resin (charged at 0.72 millimole/gram). In all cases, the first amino acid grafted was 2-Boc-aminohexadecanoic acid (2 equivalents). This made it possible to obtain constructs where the C-terminal amino acid was 2-aminohexadecanoic acid in amide form in order to avoid the presence of a charge near the hydrophobic aliphatic chain. After acetylation with acetic anhydride in basic medium, in order to block the free reactive sites, the cleavage of the N-terminal Boc and then the coupling of the first amino acid of the sequence were carried out.

All these stages were carried out manually, which made it possible to carry out very precise controls of the coupling of the pseudolipid amino acid and the first amino acid on the latter.

The coupling activator is benzotriazolyl-N-oxytriadimethylaminophosphonium (BOP) in the presence of hydroxybenzotriazole (HOBt) and diisopropylethylamine (DIEA). By virtue of this very efficient coupling method, the yield of these two coupling reactions was always greater than 99.5% despite the substantial steric hindrance due to 2-Boc-aminohexadecanoic acid.

The rest of the synthesis was carried out in a conventional manner, automatically, up to the last amino acid. At this stage, the peptidyl-resin was divided into 3 batches, treated manually:

1 batch was preserved as such;

1 batch was grafted using 2-Boc-aminohexadecanoic acid. The manual coupling (using BOP) of the latter was followed by cleavage of the N-terminal Boc and acetylation of all the amine functional groups thus exposed. This made it possible to avoid the presence of a charge near the hydrophobic aliphatic chain of the pseudolipid amino acid, 1 batch was grafted using diBoc, Nα, ε-lysine. Manual grafting (using BOP) of the latter was followed by cleavage of the two Boc groups and the manual coupling of palmitic acid (using BOP). We thus obtained peptides possessing a dipalmitoyl-lysine in the N-terminal position.

These couplings, carried out manually, were the subject of a strict control which revealed yields that were always higher than 99.5%. These results confirm the advantage of using BOP as activating agent in peptide synthesis, especially for coupling pseudolipid amino acids or for coupling to the latter. The synthesized lipopeptides were then cleaved from their support. The lipopeptides derived from the 312–327 sequence were cleaved by anhydrous hydrofluoric acid treatment. The cleavage yields are quite low, between 40 and 70%.

There are at least two explanations for these values: 1) the cleavage of a peptide grafted on a benzhydrylamine resin is never total under the usual conditions of cleavage; 2) the presence of 2-aminohexadecanoic acid, directly in contact with the resin, certainly amplified this phenomenon.

After washing twice (TFA-ether), the identity of the lipopeptides was assessed by amino acid analysis after total acid hydrolysis and, for some, by PDMS mass spectrometry. Their homogeneity was checked by thin layer chromatography on silica and analytical reverse phase HPLC.

II. Methods for Coupling Pimelautide and trimexautide

1) Method for Coupling Dimelautide (or Trimexautide) to the N-terminal End of a Peptide by Means of a Succinyl Link This method applies to the fixing of unprotected pimelautide (or trimexautide) on a peptide constructed in a solid phase, still fixed to the resin, and to protected side chains.

Both trimexautide and pimelautide (Rhone Poulenc) have two free carboxylic functional groups and a free primary amine functional group. The creation of a predetermined amide bond between the peptide and the pimelautide (or trimexautide) can only be achieved by using the pimelautide (or trimexautide) as amino partner.

The succinylation of the peptide on the resin makes it possible to make it the carboxylic partner.

Deprotection

The terbutyloxycarbonyl group, which temporarily protects the N-terminal end of the peptide on the resin, is cleaved by the action of a 40% trifluoroacetic acid solution in dichloromethane for 20 minutes with stirring.

The resin is washed with:

twice 20 ml of dichloromethane, twice 20 ml of 5% diisopropylethylamine in dichloromethane, twice 20 ml of dimethylformamide (for 3 minutes for each wash).

Succinylation

It is achieved by carrying out the coupling three times by bringing the resin of the succinylation solution into contact with:

a fivefold excess of succinic anhydride (5% solution in N-methylpyrrolidone)

diisopropylethylamine in a stoichiometric amount relative to the amines of the resin (for 20 minutes with stirring).

Activation

The activation of the carboxyl now present on the resin is carried out as follows:

the resin is subjected to the action of the activating solution (for 15 minutes at room temperature and with stirring):

BOP (benzotriazolyloxytrisdimethylaminophosphonium hexafluorophosphate): 3 excesses with respect to the carboxyls, HOBT (hydroxybenzotriazole): 3 excesses with respect to the carboxyls, diisopropylethylamine: 7 excesses with respect to the carboxyls in solution in N-methylpyrrolidone.

Washing

The solution is washed with:

3 times 30 ml of dimethylformamide, 3 times 30 ml of dichloromethane.

Coupling:

The resin is subjected to the action of the coupling solution:

pimelautide (or trimexautide): 3 excesses with respect to the activated ester of hydroxybenzotriazole, diisopropylethylamine: 3 excesses with respect to the ester, 10% dimethyl sulfoxide 90% N-methylpyrrolidone: sufficient amount to dissolve pimelautide (or trimexautide).

The saturated solution is at about 4% pimelautide or trimexautide after sonication and passage for 2 minutes at 50° C.

2) Synthesis in Solid Chase of V3GP120, 312–327 Succinyl a) N-protection of the pimelautide (or trimexautide) by the tert-butyloxycarbonyl Group 500 micromoles of pimelautide (or trimexautide) are dissolved in 10 ml of a 0.1 molar solution of carbonate buffer at pH 9.5.

10 ml of a solution of diterbutyl pyrocarbonate at 100 mmol/l are added.

A pH of between 9 and 10 is maintained for 100 hours by adding disodium carbonate.

The reaction mixture is then diluted with 10 ml of water and 10 ml of diethyl ether and the washed aqueous phase is acidified to pH 2.5 with potassium bisulfate.

An extraction with 100 ml of dichloromethane followed by evaporation of the solvent using a rotating evaporator leads to the crystallization of Boc-pimelautide (or Boc-trimexautide).

The incorporation of Boc-pimelautide (or Boc-trimexautide) by peptide synthesis in a solid phase generates two position isomers.

b) Cleavage and Purification

The cleavage of the peptide at the end of the synthesis is performed using anhydrous hydrofluoric acid.

The peptide is then purified by gel filtration and type $C_4$ reverse-phase preparative HPLC.

FIG. 1 represents the preparative HPLC spectrum at 235 nm obtained for 20 mg of lipopeptide dissolved in HCOOH.

The lipopeptide obtained is then analyzed by total acid hydrolysis, by analytical $C_4$ HPLC chromatography and mass spectrography.

Figure 2:
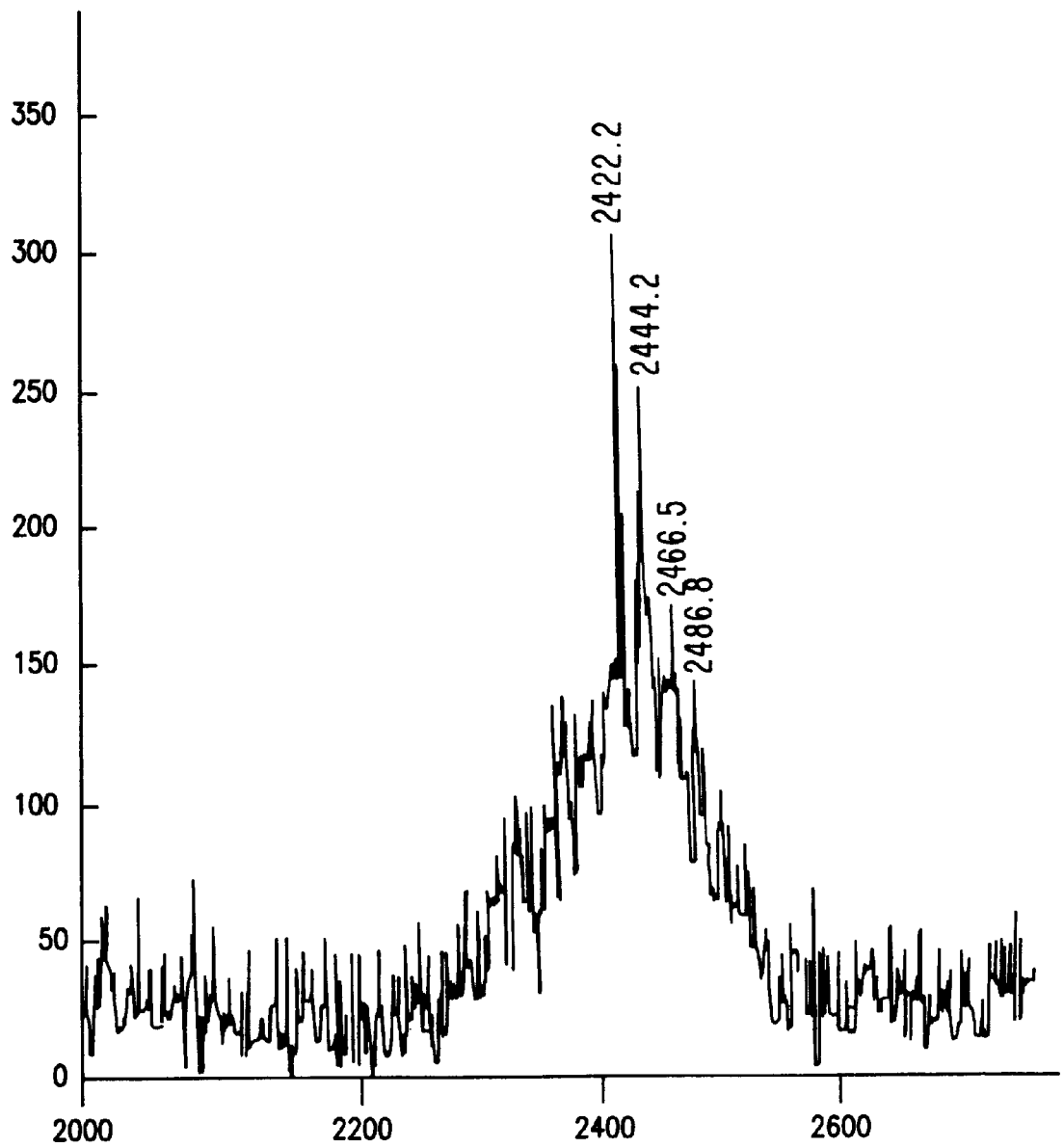
FIG. 2 represents, for its part, its mass spectrum.

FIG. 2 represents the mass spectrum. A distinct peak is observed at 2422.2 which corresponds to the mass of the lipopeptide.

Figure 3A:
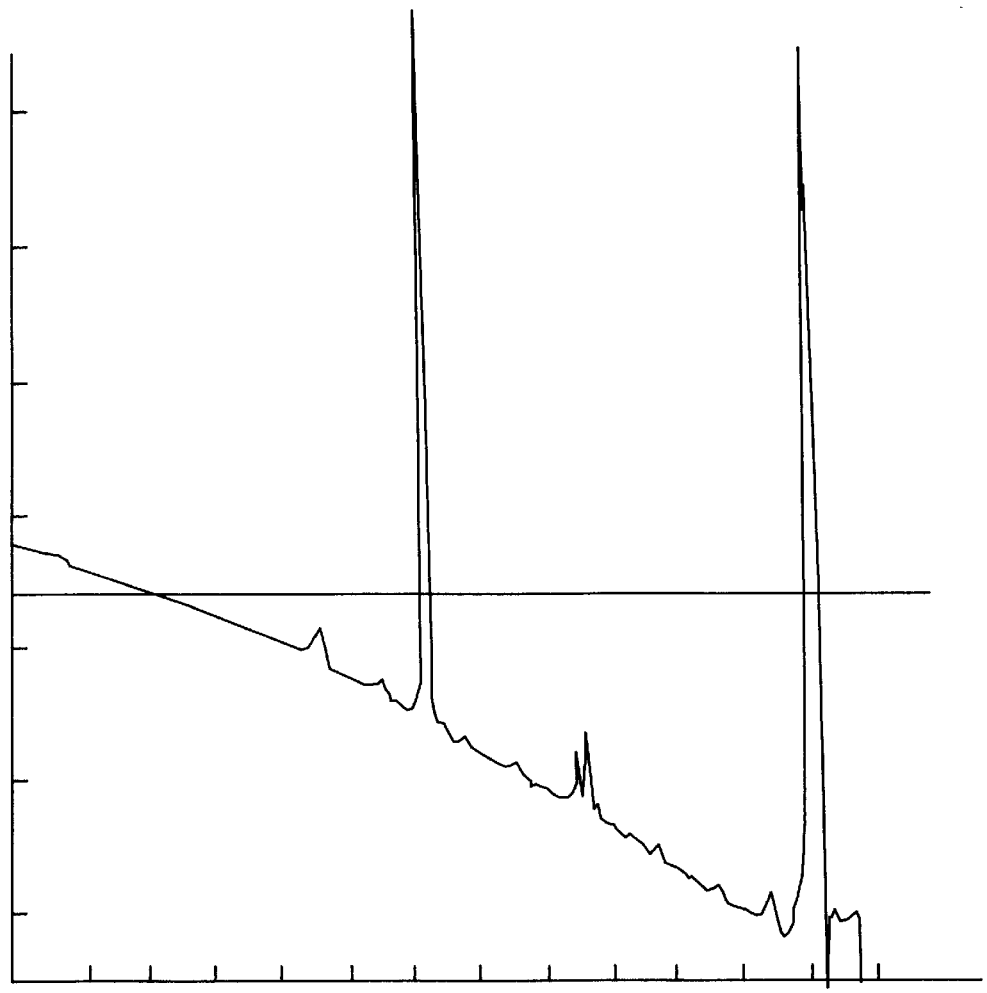
Figure 3B:
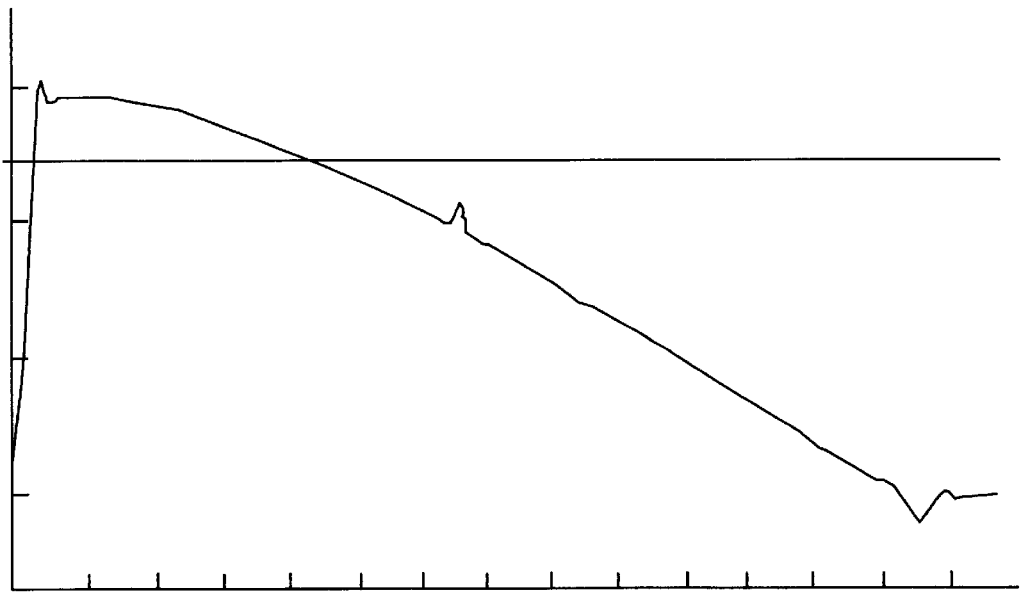

FIGS. 3a and 3b represent the analytical $C_4$ HPLC chromatography of the lipopeptide and of the control without lipopeptide respectively.

The chromatographic conditions are as follows:

solvent (A): 0.5 0/00 trifluoroacetate, gradient: solvent B: 0.75 0/00 acetonitrile 0.5% trifluoroacetate, gradient from 10% to 80% in 120 min, measurement at a wavelength of 215 nm.

During the total acid hydrolysis, the diaminopimelic acid (Dap) present in pimelautide and trimexautide constitutes a good coupling marker.

Results of the Total Acid Hydrolysis

| Amino acids | nanomoles | measured | theoretical | measured/ theoretical |
|---|---|---|---|---|
| Thr | 3.2500 | 0.97 | 1 | 0.97/1 |
| Glu | 7.1000 | 2.11 | 2 | 1.06/1 |
| Pro | 3.1800 | 0.95 | 1 | 0.95/1 |
| Gly | 10.3500 | 3.08 | 3 | 1.03/1 |
| Arg | 6.6900 | 1.99 | 2 | 1.00/1 |
| Val | 3.3900 | 1.01 | 1 | 1.01/1 |
| Ile | 9.5800 | 2.85 | 3 | 0.95/1 |
| Phe | 3.3500 | 1.00 | 1 | 1.00/1 |
| Lys | 3.5200 | 1.05 | 1 | 1.05/1 |
| Arg | 9.9200 | 2.95 | 3 | 0.98/1 |
| Dap | 3.500 | 1.05 | 1 | 1.05/1 |

EXAMPLE 3

Immunization against the peptide NP 147–158 (SEQ ID NO:1).

The immunizations of mice are carried out as follows:

Immunizations

The mice were injected with the lipopeptide preparations intraperitoneally (i.p.) or subcutaneously (S.C.), with or without adjuvant.

At least two injections (at intervals of 8 to 30 days) are necessary in order to obtain CTLs.

Each injection contains $5 \times 10^{-8}$ mole of lipopeptide.

Detection of the CTLs 8 to 21 days after the last injection, the spleen of the immunized mice was removed, the splenocytes of these mice were cultured in vitro in an amount of $5 \times 10^6$ splenocytes/2 ml of conventional culture medium (DMEM+ 10% FeS+pyruvate+nonessential amino acids +-β-2-mercaptoethanol) containing 5 μM of the peptide corresponding to that involved in the lipopeptide construction.

From the 5th day of the in vitro culture, the activity of the CTLs may be detected by the conventional test of $^{51}Cr$ release (Martinon et al., J. Immunol., 142;3489–3494, 1989).

The CTL activity is tested against some syngenic target cells in the presence of the peptide (NP 147–158 R⁻,P₃CSS. PepNP or L₁-Pep.NP) or against some syngenic target cells infected by the influenza A virus.

The results obtained are summarized in Table I. The first part of the table relates to the results already obtained with the whole influenza virus, the NP 147–158 R protein of the influenza virus (SEQ ID NO:1) and the P3CSS-PEPNP lipopeptide, which consists of the NP 147–158 peptide (SEQ ID NO:1) coupled to tripalmitoyl-S-glyceryl-cysteinylserylserine (DERES et al. previously mentioned).

The second part of the table relates, on the one hand, to the immunization trials carried out with liposomes containing the NP 147–158 peptide and with the lipopeptides L1, L2 and L3. These lipopeptides are molecules containing a peptide part (NP 147–158) and a lipid part, respectively. The lipopeptides L1, L2 and L3 are therefore of the following formulae The cytolytic activities after 5 days, 12 days and more than 21 days show that a very high activity is obtained for the lipopeptide L1 compared to the other trials carried out.

EXAMPLE 4

Immunization by CB1, CB2 and CB3 against the ENV 312–327 peptide.

This peptide is a protein fragment encoded by the ENV gene of the HIV virus.

The experimental procedures are identical to those described in Example 3.

Table II summarizes the results obtained.

In this table, CB1 (SEQ ID NO:2), CB2 (SEQ ID NO:2) and CB3 (SEQ ID NO;2) correspond to lipopeptides formed from the peptide derived from the ENV protein and a lipid. The formulae of CB1, CB2 and CB3 are as follows:

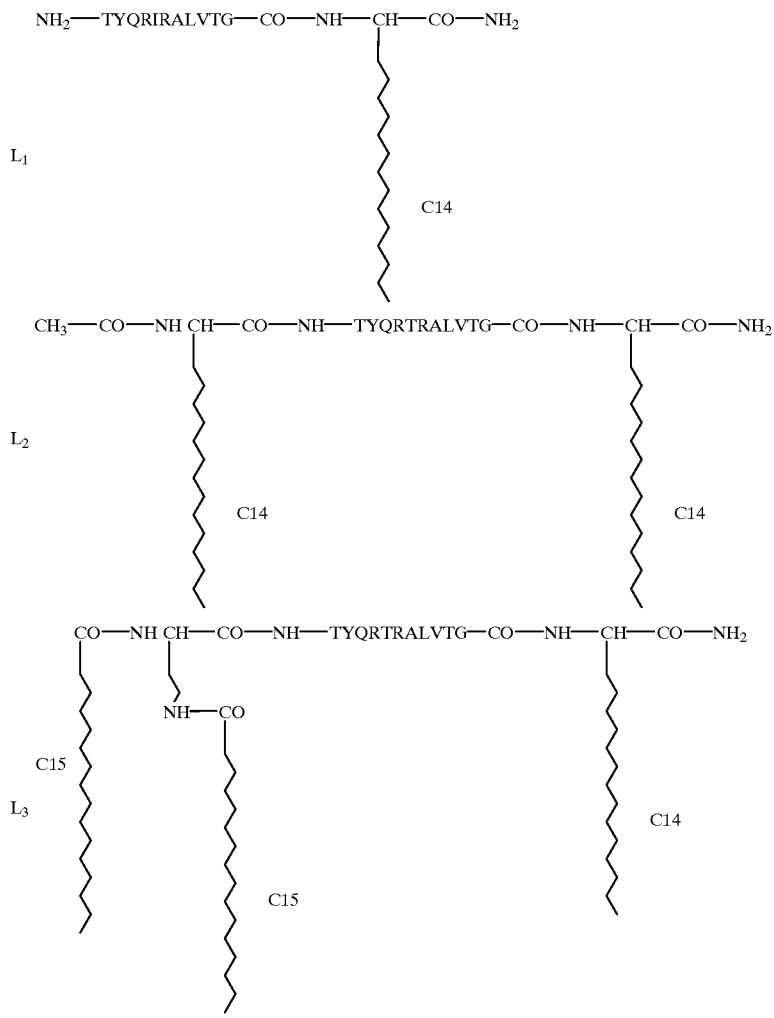

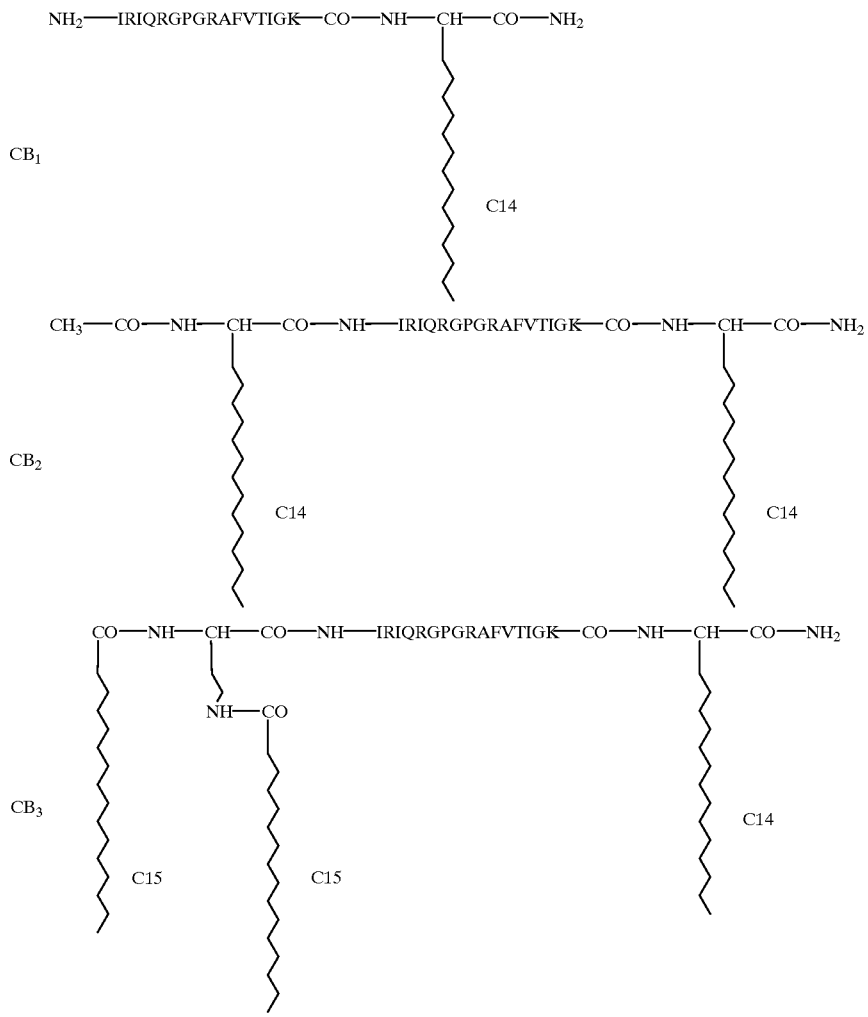

The results in Table II show a substantial activity for one of the lipopeptides (CB1).

EXAMPLE 5

Immunization against the peptide ENV 302–335.

This peptide is the 302 to 335 fragment of the ENV protein (SEQ ID NO:3) of the HIV virus.

The experimental procedures are identical to those described in Example 3.

The results are shown in Table III. The formulae of the lipopeptides $CB_6$ (SEQ ID NO:3), $CB_7$ (SEQ ID NO:3) and $CB_8$ (SEQ ID NO:3) are as follows:

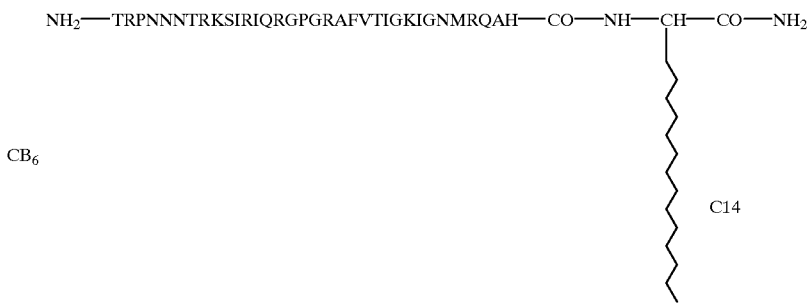

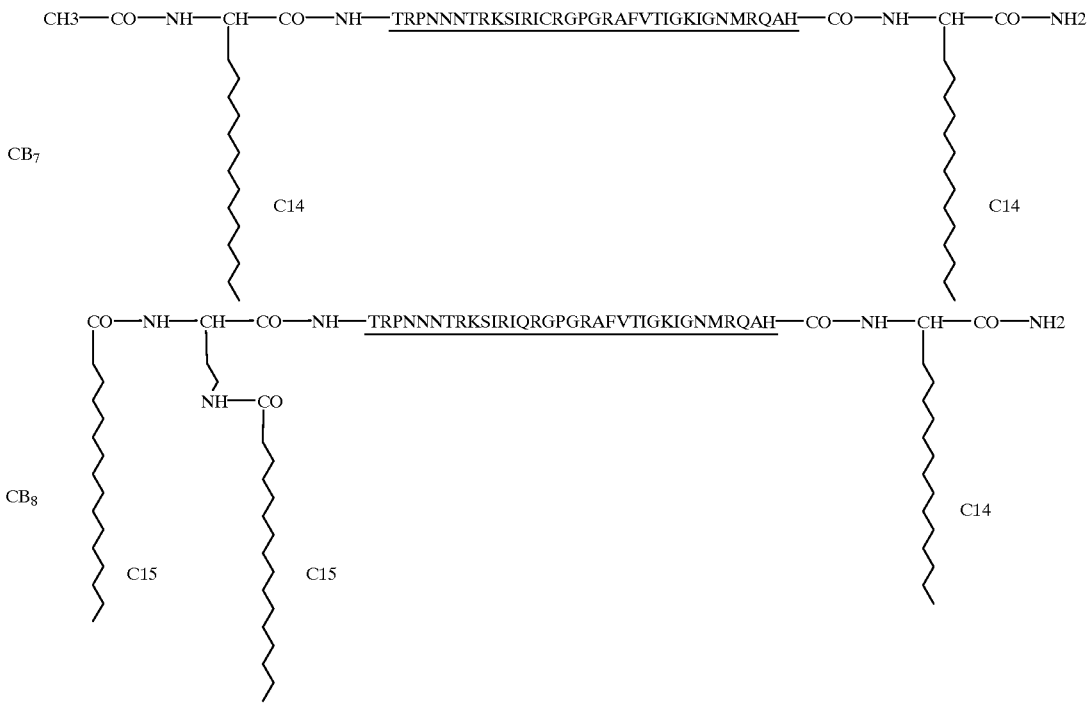

It can be observed in Table III that the two lipopeptides, $CB_6$ and $CB_7$, show cytolytic activities substantially higher than the control.

EXAMPLE 6

Immunization against the peptide ENV 312–327 by CB1, CB4, CB5, CB17, CB19, CB21 and CB25.

The experimental procedures are substantially identical to those described in example 3.

The table IV summarizes the results obtained.

The formula of $CB_1$ is indicated in example 4.

The formulae of CB4 (SEQ ID NO:2), CB5 (SEQ ID NO:2), CB17 (SEQ ID NO:3), CB19 (SEQ ID NO:2), CB21 (SEQ ID NO:3) and CB25 are as follows:

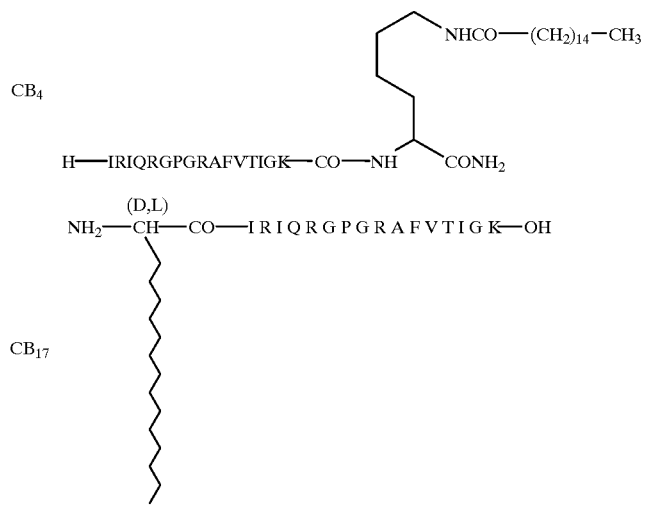

-continued

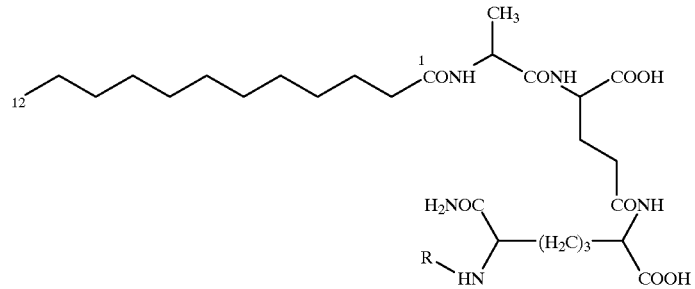

CB 5 = R = —CO—(CH₂)₂—CONH—IRIQRGPGRAFVTIGK—OH

CB 19 = R = CO—CH₂—NH—CO (CH₂)₂—CONH—IRIQRGPGRAFVTIGK—OH

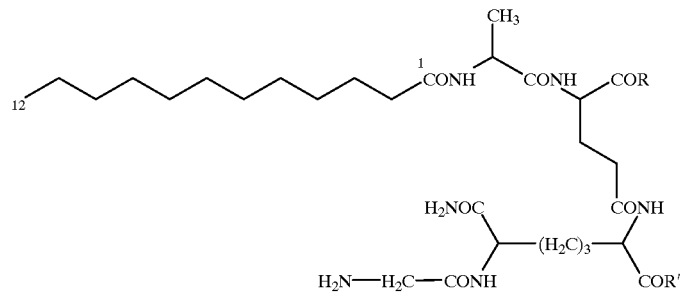

CB 21 Mixture of A: R = OH
R' = NH—IRIQRGPGRAFVTIGK—OH
B: R = NH—IRIQRGPGRAFVTIGK—OH
R' = OH

CB₂₅

EXAMPLE 7

Materials and Methods

Sequences of peptides and lipopeptides

Peptides from NEF protein were as follows:

```
    LP1 101-126 (S-V-R-P-K-V-P-L-R-A-M-T-Y-K-L-A-I-D-M-    (SEQ ID NO:4)
S-H-F-I-K-E-K)

LP2 125-147 (E-K-G-G-L-E-G-I-Y-Y-S-A-R-R-H-R-I-L-D-    (SEQ ID NO:5)
M-Y-L-E),

LP3 155-178 (D-W-Q-D-Y-T-S-G-P-G-I-R-Y-P-K-T-F-G-W-    (SEQ ID NO:6)
L-W-K-L-V),

LP4 201-225 (S-K-W-D-D-P-W-G-E-V-L-A-W-K-F-D-P-T-L-    (SEQ ID NO:7)
A-Y-T-Y-E-A) and LP5 221-247 (Y-T-Y-E-A-Y-A-R-Y-P-E-E-L-E-A-S-Q-A-C-    (SEQ ID NO:8)
Q-R-K-R-L-E-E-G).
```

In addition, two GAG SIV epitopic peptides.

```
    LP6 165-195 (K-F-G-A-E-V-V-P-G-F-Q-A-L-S-E-G-C-T-P-    (SEQ ID NO:9)
Y-D-I-N-Q-M-L-N-C-V-G-D) and LP7 246-282 (Q-I-Q-W-M-Y-R-Q-Q-N-P-I-P-V-G-N-I-Y-R-    (SEQ ID NO:10)
R-W-I-Q-L-G-L-Q-K-C-V-R-M-Y-N-P-T-N-)
``` were synthesized.

Synthesis of p-methyl-BHA-N-BOC-HDA Resin

N-tert-butyloxycarbonyl-amino hexadecanoic acid (Boc-Hda) was synthesized as described previously (Martinon et al.1992.J.Immunol.149: 3416). This molecule was manually coupled to the p-methyl-benzhydrylamine resin according to the BOP/HOBt procedure (Le-Nguyen et al. 1987.J. Chem. Soc.Perkin Trans. I:1915). All lipopeptides were thus obtained with a carboxamide C-terminal end.

Synthesis of Lipopeptides

The lipopeptides were synthesized using the solid phase synthesis according to the "Boc-Benzyl strategy" (Merrifield, 1963. J.Amer.Chem.Soc.85: 2149) in an automated Applied Biosystems 470A peptide synthesizer (Applied Biosystems. Foster City, USA), starting on 0.5 mmol of Boc-Hda-resin. Tert-butyloxycarbonyl (t-Boc) protected amino acids were purchased from the Peptide Institute (Osaka, Japan). The activation procedure was the dicyclohexylcarbodiimide/hydroxybenzotriazole method. Side chain functional groups were protected as follows: serine (benzyl); threonine (benzyl); cysteine (S-paramethylbenzyl); aspartic (O-cyclohexyl); glutamic (O-cyclohexyl); tryptophane (formyl); histidine ($N^{-im}$ dinitrophenyl); tyrosine (2,6-dichloro-benzyl); arginine (tosyl); lysine (N-2-chlorobenzyloxycarbonyl) and methionine (sulfoxide). Coupling of each amino acid residues was followed by a capping step with acetic anhydride.

Cleavage and Deprotection of Lipopeptidyl-resins

Before the hydrogen fluoride (HF) cleavage procedure (low and/or high HF) (Tam et al.1983. J.Am.Chem.Soc.105: 6442), histidine ($N^{-im}$ dinitrophenyl) containing lipopeptides were stirred for one night at room temperature in a N,N-dimethylformamid/beta mercaptoethanol/N-ethyldiisopropyla-min (70/20/10:v/v/v) solution in order to remove the dinitrophenyl group. At the end of the HF cleavage, carried out with a Teflon-Kel F apparatus (Asti, Courbevoie, France), the lipopeptides were extracted from the resin with pure TFA and precipitated in a large volume of cold ether. After centrifugation, the precipitate was dissolved either in a 5% acetic acid solution or in a 5% ammonia solution in regard to their isoelectric pH.

The amino acid composition of each crude lipopeptide was determined by using an automated Beckman 6300 amino acid analyser (Beckman, Calif., USA) after total acid hydrolysis at 110° C. for 24 hours in 6M HCl.

Purification and Characterization of Lipopeptides by RP-HPLC

Lipopeptides were purified by RP-HPLC on a Vydac C4 7 $\mu$m 300A column (9×300 mm) using a acetonitrile-water-0.05% TFA solvent system. The lipopeptides were eluted from the column using a 60 minutes gradient from 24% to 60% acetonitrile. The flow rate was 2 ml/mn. Lipopeptides were characterized by amino acid analysis and molecular mass determination by Plasma Desorption Mass Spectrometry (PDMS) on a Bio ion 20 device (Applied Biosystems, Sweden) (Chowdhury and Chait.1989.Anal.Biochem. 180: 387). The tubes containing pure lipopeptides were pooled and lyophilyzed.

Animals and Protocol of Immunizations

Twelve rhesus macaques (Macaca mulatta) were inoculated subcutaneously with a mixture of 7 lipopeptides (500 $\mu$g of each) in incomplete Freund adjuvant. Three immunizations were performed respectively at day 0.30 and 60. No side effect was observed except slight and transient erythema at the site of injection in macaque RS4.

Lymphocyte Preparation

Peripheral blood mononuclear cells (PBMC) were isolated by density gradient centrifugation on lymphocyte separation medium (Flow Laboratories, Glasgow, United Kingdom) and were either used immediately or stored at −180° in liquid nitrogen.

Generation of the CTL Lines

PBMC from rhesus macaques were cultured at $2.10^6$ cells/ml in 24-well microtiter plates in culture medium consisting of RPMi 1640 supplemented with penicillin (100 U/ml), streptomycin (100 $\mu$g/ml), L-glutamine (2 mM), nonessential amino acids (1%), sodium pyruvate (1 mM), HEPES (N-2-hydroxyethylpiperazine-N'-2-ethanesulfonic acid) buffer (10 mM), beta-mercaptoethanol ($2.10^{-5}$M), and 10% heat-inactivated human AB serum. Mixture of the 7 peptides was added in each well at a concentration of 5 $\mu$M. After 3 days, 10 IU/ml interleukin-2 (IL.2) (Boehringer, Mannheim) was added. At Days 7 and 14, cultures were stimulated by fresh autologous PBMC previously pulsed for 2 hours with the pool of the 7 peptides (5 $\mu$M), washed and irradiated (4,000 rads)(ratio effector: stimulator=1:3). In some experiments, effector cells have been stimulated by autologous SIV-infected cells prepared as follows. Briefly PBMC were cultured with ConA during 3 days and then infected with SIV ($10^2$ TCID50 for $10^6$ cells). After one week, these cells were washed and irradiated (10,000 rads) and served as stimulator (ratio effector: stimulator=1:1).

Phenotypic Analysis of T-cell Lines

The T-cell lines were phenotyped the day of the chromium release test (CRT) by incubating cells with fluorescein isothiocyanate-conjugated anti-CD4 (OKT4; Ortho Diagnostic Systems. Raritan, N.J.) and phycoerythrin-conjugated anti-CD8 (Leu-2a; Becton-Dickinson, Mountain, View, Calif.) monoclonal antibodies for 10 minutes at room temperature, washing once with phosphate-buffered saline. All cells were examined for percent positive-staining cells on an EPIC CS flow cytometer (Coulter).

Cell Fractionation

PBMC were incubated at $10^7$ cells/ml with either OKT4 (2 $\mu$g) or Leu 2a (1 $\mu$g) for 30 minutes at 4° C. After incubation with OKT4 or Leu 2a, CD4+ or CD8+ cells were eliminated by magnetic separation with immunomagnetic beads (Dynabeads, Dynal, Oslo, Norway). The cells were then washed with culture medium.

In Vitro Transformation of B Cell Lines

B-lymphoblastoid cell lines (LCL) were generated by incubating serial dilutions of PBMC with supernatant of S 594, S 594 , kindly provided by N. Letvin, is a cell line producing the immortalizing baboon herpes virus (Herpes virus papio). B-LCL were then cultured in culture medium supplemented with 10% foetal calf serum.

Recombinant Vaccinia Viruses

Sequences encoding the NEF and the GAG p55 proteins were inserted into vaccinia virus, which served to infect target cells. The wild-type vaccinia virus, strain Copenhagen, was used as a control. All these constructions were made by Transgene, Strasbourg, France.

Chromium Release Test (CRT)

To obtain target cells presenting SIVmac gene products, B-LCL were incubated at a concentration of $10^6$ cells/ml with recombinant vaccinia virus (20 pfu per cell) for 18 hours at 37° C. in a 5% $CO_2$ humidified atmosphere. To sensitize target cells with peptides, the peptides were incubated overnight at a concentration of 20 $\mu$M with $10^6$ B-LCL under the same conditions. B-cells were then washed and labelled with 100 $\mu$Cl or $Na_2$ $^{51}CrO_4$ (Amersham, UK) for 1 hour, washed twice and used as target cells. $^{51}Cr$ release assay was performed in V-bottomed 96-well microtiter plated. The cytolytic activity of anti-SIV cell lines was measured by mixing $5\times10^3$ $^{51}Cr$ labelled target cells with effector cells at various E/T ratios in a final volume of 0.2 ml/well. Plates were incubated for 4 hours at 37° C. after which 0.1 ml of supernatant was harvested from each well and analysed by a gamma counter. Spontaneous release was determined after incubating target cells with medium alone and never exceeded 20% of the total $^{51}$Cr incorporation. Results were expressed as specific chromium release: 100× (experimental cpm- spontaneous cpm)/(maximum cpm— spontaneous cpm).

Results:

1- CTL activities have been found in 7 macaques

CTL activity has been induced in 7 macaques, directed against a NEF peptide in 5, and against a GAG peptide in the remaining 2 (table V). Six macaques recognized a single peptide, only one macaques, RS20 recognizing 2 different NEF peptides.

Among the NEF peptides, NEF 155–178 (SEQ ID NO:6) appears highly immunogenic since it was epitopic for CTL in 3 macaques (RS6, RS17, RS20). NEF 201–225 (SEQ ID NO:7) was recognized by 2 macaques (RS21, RS23). In contrast, NEF 125–147 (SEQ ID NO:5) was recognized by only one macaque (RS20). Similarly, the two GAG peptides were recognized respectively by macaques RS4 (165–195) and RS7 (246–281). Finally, two of the NEF peptides, NEF 101–125 (SEQ ID NO:4) and NEF 221–247 (SEQ ID NO:8) have never been recognized.

Cytolytic activities were usually detected after 3 in vitro stimulations (day 21 of the culture) although some activities have been occasionally observed after only 1 or 2 in vitro stimulations.

Figure 4A:
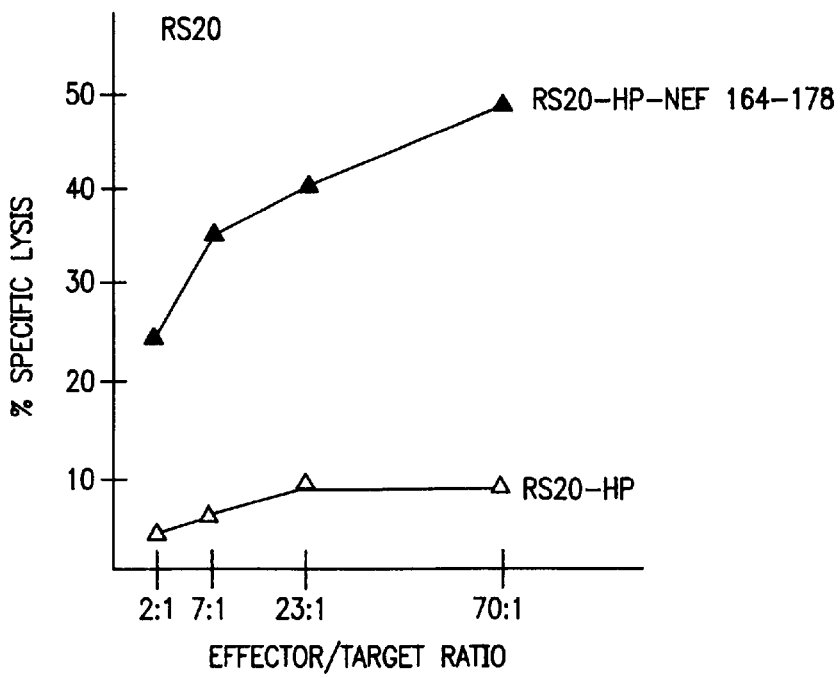
FIG. 4 represents the specific cytolytic activity of an anti-peptide NEF.164–178 CTL from macaque RS20.
Figure 4B:
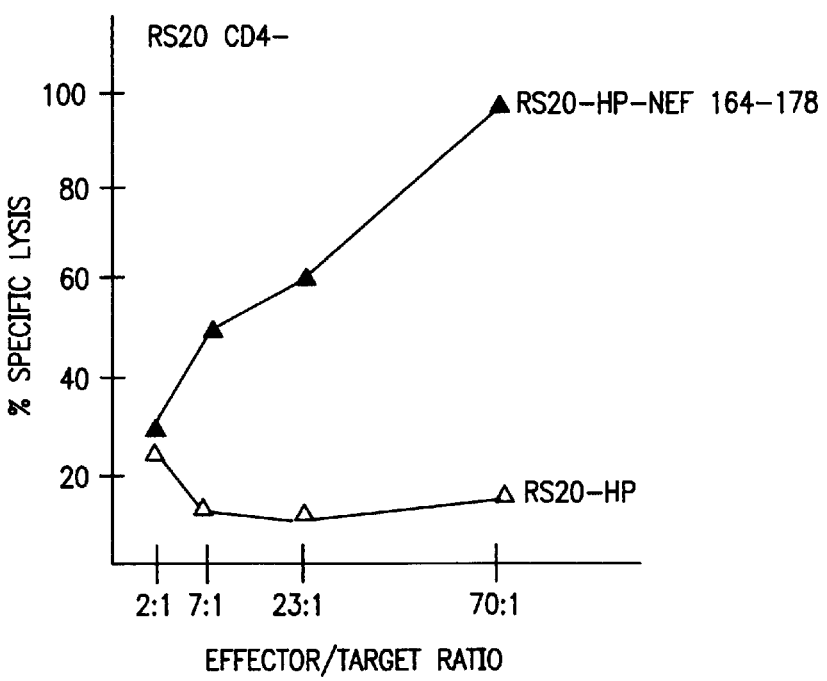
Figure 4C:
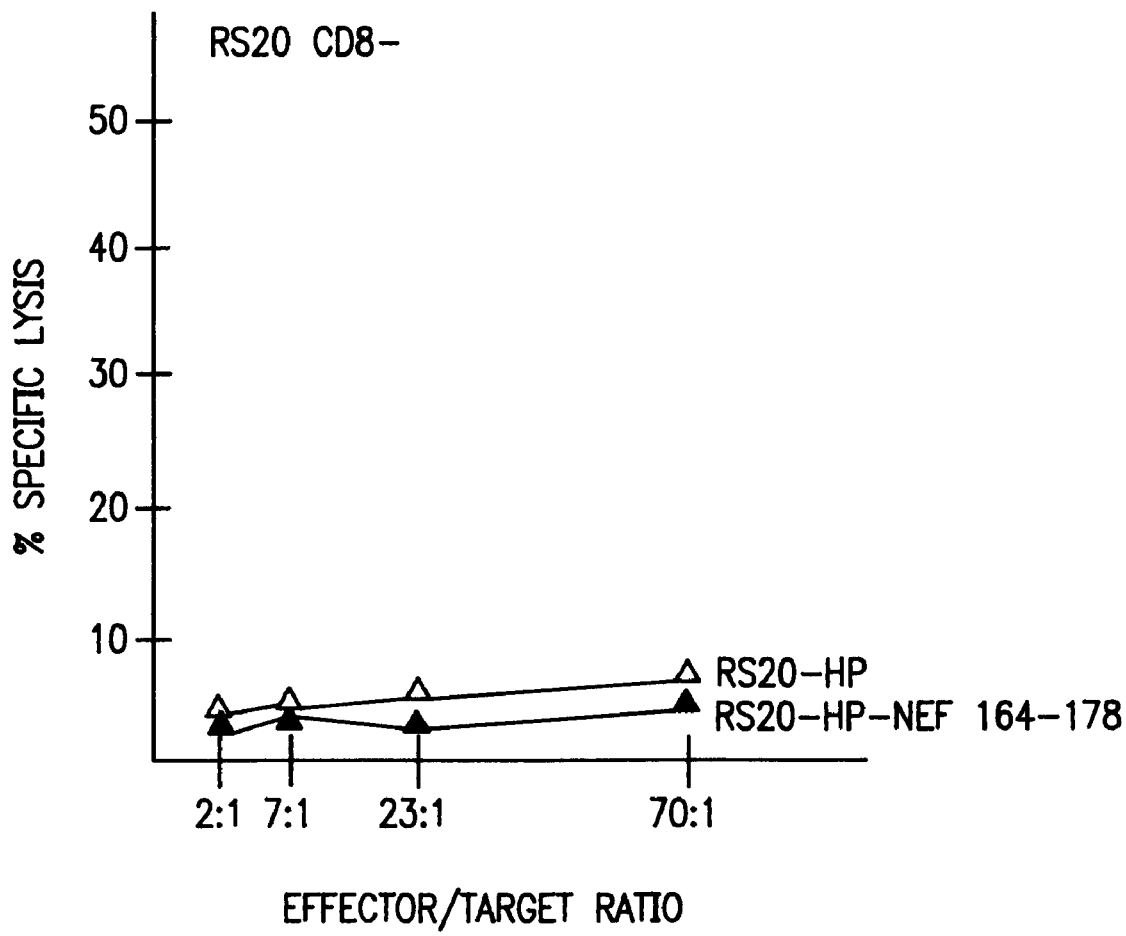

At day 21, the cell lines evidenced a predominantly CD8 phenotype (on average 35% CD4+ cells and 50% CD8+ cells )(table V) suggesting that the cytotoxic activities were mediated by CD8+ lymphocytes. This was confirmed by depletion experiments, CTL activity disappearing after elimination of these cells, whereas CD4 depletion has no effect on the lysis, as illustrated in FIG. 4 for macaque RS20. This figure represents the specific cytolytic activity of anti-peptide NEF 164–178 (SEQ ID NO:11) CTL from macaque RS20. Effector cells were unfractionated PBMC (4a), or PBMC depleted of CD4+ cells by treatment with a monoclonal antibody anti-CD4 plus complement (4b), PBMC depleted of CD8+ cells by treatment with an anti-CD8 monoclonal antibody (MoAb) bound to magnetic beads at the time of CRT (4 c). Target cells were autologous B-LCL alone or incubated with NEF peptide 164–178.

2-No CTL Activity was found before Immunization

To assess the in vivo priming of macaques by lipopeptides and to discard a possible in vitro induction of CTL responses during the culture, the cells of 5 responding macaques have been tested (RS4, RS17, RS20, RS21, RS23) sampled before any in vivo immunization. They were stimulated in vitro with the pool of peptides. In most cases, no cellular growth was observed and massive cell death prevented from performing the CRT. In a few cases, cell lines were obtained. They were of the CD4+ type and no cytotoxic activity was observed.

Figure 5B:
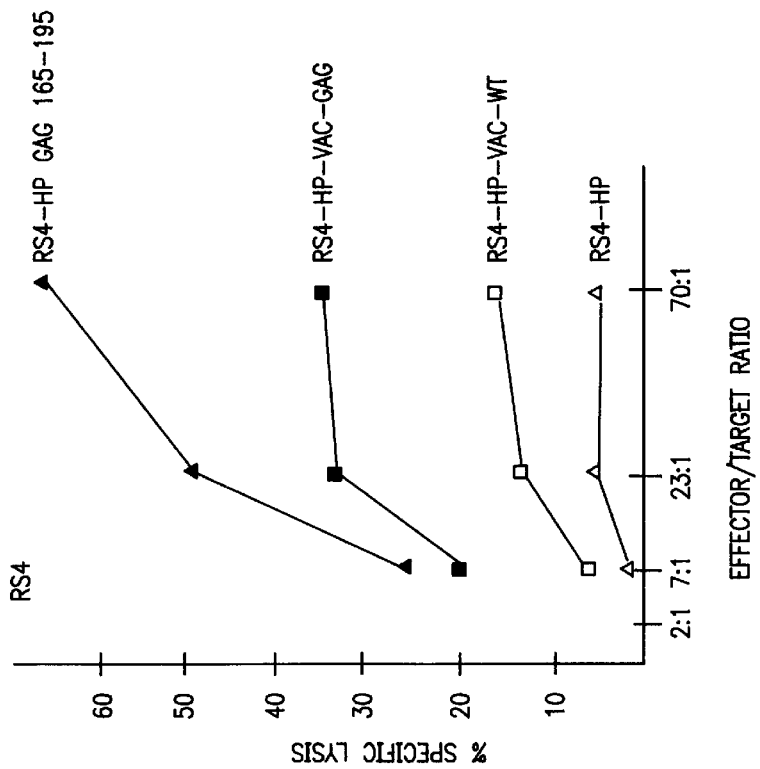
FIG. 5 illustrates the cytolytic activity of RS4 effector cells stimulated by autologous PBMC sensitized with various peptides.
Figure 5A:
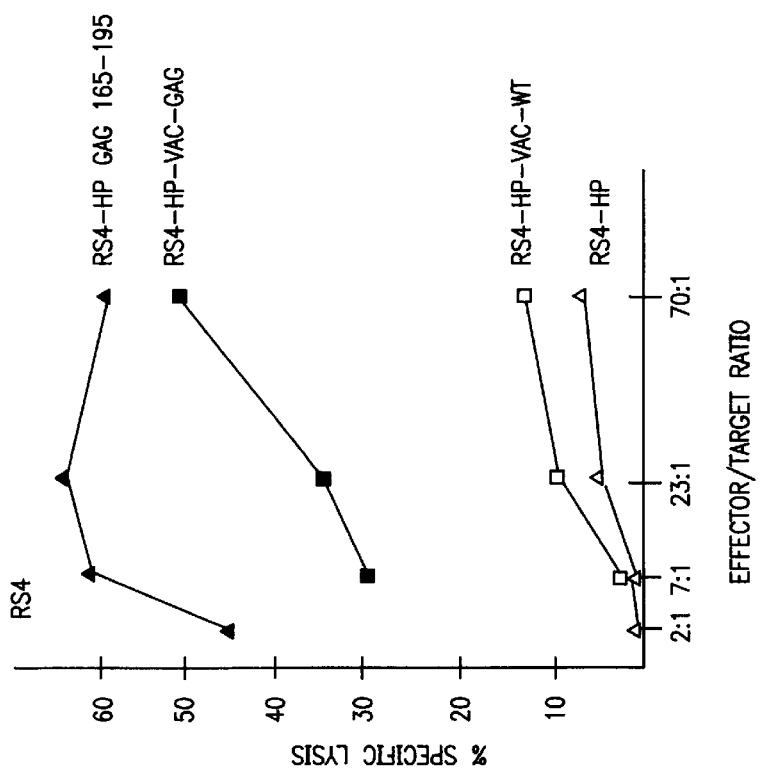

3-NEF and GAG Specific CTL Recognized Naturally Processed Peptides from NEF or GAG Proteins It was important to determine whether or not the CTL of responder macaques would be capable to recognize not only the immunizing synthetic peptides but also the naturally processed peptides in infected cells. To answer this question. Effector cells were stimulated by autologous PBMC sensitized with the mixture of peptides (5a) or by autologous SIV infected blasts (5b). Target cells were autologous B-LCL alone, incubated with peptide GAG 165–195, infected with a wild type vaccinia virus or with GAG recombinant vaccinia virus (Vac-GAG).

a) It has demonstrated at first that CTL induced by lipopeptides could lyse Vac-NEF or Vac-GAG infected autologous target cells as illustrated for macaque RS4 in FIG. 5a. Similar cytolytic activities against Vac-NEF or Vac-GAG infected cells were regularly demonstrated in all the 7 responder macaques (Table VI).

b) PBMC from immunized animals have been stimulated by autologous SIV-infected cells. The CTL generated in these experiments were able to lyse peptide sensitized target cells as well as target cells infected with the corresponding recombinant vaccinia virus as shown in FIG. 5b for macaques RS4.

c) It must be also emphasized that in three responder macaques, shorter 15-mer peptides were defined as epitopes and were identical to epitopic peptides previously described in SIV-infected macaques (Table VII) (Bourgault et al. 1992.J.Virol.66: 750, Yamamoto et al.1990. J.Immunol.144: 3385).

4. Kinetics of in Vivo CTL Responses

Cytotoxic activities were systematically detected in all responder macaques after 3 immunizations. However, in 3 macaques (RS4, RS17 and RS20), CTL were already found after two immunizations.

Interestingly, after having been detected, these cytotoxic responses always persisted for at least 13 months after the last immunization in the two macaques (RS4 and RS20) which have the longest follow-up after immunization, confirming the presence of long lasting CTL memory cells in immunized animals.

Conclusion

These CTL found in these experiments are clearly primed in vivo.

These results demonstrate that naturally processed peptides are recognized at the stimulator as well as at the effector stages of the immune response by lipopeptides induced CTL.

A major interest of vaccination with lipopeptides found in these experiments is the persistence in peripheral blood of a detectable CTL precursor activity for at least 10 months. Humoral immune response usually declines quickly after immunization although memory B cells persist at a low level and can be further reactivated. After immunization, one expected a decrease in CTL activity with homing of memory CTL within lymphoid organs and few circulating memory cells. The persistence of a strong activity in circulating PBMC suggest a high frequency of memory CTL precursors.

Interests of lipopeptidic vaccines are multiple. Lipopeptides are safe, without side effects, and the protocol of vaccination could be easily applicable to humans. Moreover, the response will not be hampered by a preexisting immune response against the vector as observed with recombinant viruses (Cooney, E. L. et al. 1991. Lancet 337: 567). In addition, lipopeptides allow the induction of antibodies; anti NEF and GAG antibodies were detected in this study but are unlikely to be efficient for protection. However, neutralizing antibodies have been obtained in mice by immunization against ENV (HIV1)—derived lipopeptides. Therefore, the association of lipopeptides inducing CTL to other lipopeptides capable to generate antibodies should result in efficient protection.

TABLE I

ANTI-NP 147-158R PEPTIDE (SEQ ID NO: 1) IMMUNIZATIONS (influenza virus)

| In vivo injection | In vitro stimulation | Target | Cytolytic activity d5 | d12 | ≧d21 |
|---|---|---|---|---|---|
| 0 | NP.147–158R⁻ | NP.147–158R⁻[a] | – | – | ++ |
|  |  | Influ. virus[b] |  |  | (+) |
| Influ. virus | NP.147–158R⁻ | NP.147–158R⁻ | (++) | (++) | (+++) |
|  |  | Influ. virus | (++) | (++) | (+++) |
| NP.147–158R⁻ | NP.147–158R⁻ | NP.147–158R⁻ | (–) | – | + |
|  |  | Influ. virus | (–) |  |  |
|  | Influ. virus | Influ. virus | (–) |  |  |
| P₃CSS-Pep.NP | NP.147–158R⁻ | NP.147–158R⁻ | (++) |  |  |
|  |  | Influ. virus | (++) |  |  |
|  |  | P₃CSS-Pep.NP. | (++) |  |  |
| LIPOSOME-Pep.NP. |  |  |  |  |  |
| [1* s.c. syntex][c] | NP.147–158R⁻ | NP.147–158R⁻ | – | – |  |
| [1* i.p.] | NP.147–158R⁻ | NP.147–158R⁻ | – | – |  |
| [2* s.c. syntex] | NP.147–158R⁻ | NP.147–158R⁻ | – | ++ |  |
| [2* i.p.] | NP.147–158R⁻ | NP.147–158R⁻ | – | ++ |  |
| LIPOPEPTIDES-Pep.NP. |  |  |  |  |  |
| L1-Pep.NP.[2* i.p.] | NP.147–158R⁻ | NP.147–158R⁻ | – | +++ |  |
|  |  | Influ. virus | – |  |  |
|  |  | L1-Pep.NP. | +++ | +++ |  |
| L2-Pep-NP. [2* i.p.] | NP.147–158R⁻ | NP.147–158R⁻ | – | – |  |
|  |  | Influ. virus | – | – |  |
|  |  | L1-Pep.NP. | – | – |  |
| L3-Pep.NP. [2* i.p.] | NP.147–158R⁻ | NP.147–158R⁻ | – | – |  |
|  |  | Influ. virus | – | – |  |
|  |  | L1-Pep.NP. | – | – |  |

The results in brackets have already been published.

[a] syngenic target cells in the presence of 3 μm of the peptide NP.147–158R
[b] syngenic target cells infected by the virus influenza A
[c] liposomes loaded with peptide NP 147–158R.

TABLE II

ANTI-ENV.312–327 PEPTIDE (SEQ ID NO: 2) IMMUNIZATIONS (HIV-BRU) by CB₁, CB₂ and CB₆

| In vivo injection | In vitro stimulation | Target | Cytolytic activity d5 | d12 | ≧d12 |
|---|---|---|---|---|---|
| 0 | ENV.312–327 | ENV.312–327[a] | – | – | ++ |
|  |  | Vac-env[b] | – | – | – |
|  | CBI | ENV.312–327 | – |  | – |
| Vac-env | ENV.312–327 | ENV.312–327 | (++) |  |  |
|  |  | Vac-env | (++) |  |  |
| ENV.312–327 | ENV.312–327 | ENV.312–327 | – | – | ++ |
|  |  | Vac-env | – | – | – |
| LIPOPEPTIDES-ENV. 312–327 |  |  |  |  |  |
| CB1 [1* i.p.] | ENV.312–327 | ENV.312–327 | – |  |  |
| CB1 [2* i.p.] | ENV.312–327 | ENV.312–327 | +++ | +++ | +++ |
|  |  | Vac-env | +++ | +++ | +++ |
| CB1 [1* s.c.syntex] | ENV.312–327 | ENV.312–327 | – |  |  |
| CB1 [2* s.c.syntex] | ENV.312–327 | ENV.312–327 | ++ |  |  |
|  |  | Vac-env | ++ |  |  |
| CB2 [2* i.p.] | ENV.312–327 | ENV.312–327 | – |  | ++ |
|  |  | Vac-env | – |  | ++ |
| CB3 [2* i.p.] | ENV.312–327 | ENV.312–327 | – |  | – |
|  |  | Vac-env | – |  | – |

[a] syngenic target cells in the presence of 3 μM of peptide INV 312–327
[b] syngenic target cells infected by a vaccine virus allowing the expression of the gene env of HIV

TABLE III

ANTI-ENV.302–335 PEPTIDE (SEQ ID NO: 3) IMMUNIZATIONS (HIV-BRU)

| In vivo injection | In vitro stimulation | Target | Cytolytic activity | | |
|---|---|---|---|---|---|
| | | | d5 | d12 | ≧d21 |
| ENV.302–336 | ENV.302–336 or ENV.312–327 | ENV.312–327[a] | | – | – |
| LIPOPEPTIDES-ENV.302–335 | | | | | |
| CB6 [2* i.p.] | ENV.302–336 or ENV.312–327 | ENV.312–327[a] Vac-env[b] | | ++ | +++ |
| CB7 [2* i.p.] | ENV.302–336 or ENV.312–327 | ENV. 312–327 Vac-env | | ++ | +++ |
| CB8 [2* i.p.] | ENV.302–336 or ENV.312–327 | ENV.312–327 Vac-env | | – | – |

[a] and [b]: of Table II

TABLE IV

Anti-ENV.312–327 peptide (SEQ ID NO: 2) immunizations by $CB_1$, $CB_4$, $CB_{17}$, $CB_{19}$, $CB_{21}$, $CB_{25}$ and $CB_5$

| in vivo injection | in vitro stimulation | target | cytotoxic activity | |
|---|---|---|---|---|
| | | | <14 days | >21 days |
| CB1 (2 × s.c.) | ENV 312–327 | ENV 312–327[a] | +++ | +++ |
| | | Vac-ENV[b] | +++ | +++ |
| | | CB1 | +++ | +++ |
| CB4 (2 × i.p.) | ENV 312–327 | ENV 312–327 | +++ | +++ |
| | | Vac-ENV | +++ | +++ |
| CB17 (2 × i.p.) | ENV 312–327 | ENV 312–327 | – | ++ |
| | | Vac-ENV | – | + |
| CB19 (2 × i.p.) | ENV 312–327 | ENV 312–327 | + | ++ |
| | | Vac-ENV | – | + |
| CB21 (2 × i.p.) | ENV 312–327 | ENV 312–327 | ++ | +++ |
| | | Vac-ENV | ++ | +++ |
| CB25 (2 × i.p.) | ENV 312–327 | ENV 312–327 | +++ | NT |
| | | Vac-ENV | ++ | |
| CB25 (2 × i.p.FIA) | ENV 312–327 | ENV 312–327 | ++ | NT |
| | | Vac-ENV | + | |
| CB25 (3 × i.p.) | ENV 312–327 | ENV 312–327 | +++ | NT |
| | | Vac-ENV | ++ | |
| CB25 (3 × i.p.FIA) | ENV 312–327 | ENV 312–327 | ++ | NT |
| | | Vac-ENV | ++ | |
| CB25 (2 × s.c.) | ENV 312–327 | ENV 312–327 | +++ | NT |
| | | Vac-ENV | ++ | |
| CB25 (2 × s.c.FIA) | ENV 312–327 | ENV 312–327 | +++ | NT |
| | | Vac-ENV | +++ | |
| CB25 (3 × s.c.) | ENV 312–327 | ENV 312–327 | +++ | NT |
| | | Vac-ENV | ++ | |
| CB25 (3 × s.c.FIA) | ENV 312–327 | ENV 312–327 | +++ | NT |
| | | Vac-ENV | +++ | |
| CB5 (2 × i.p) | ENV 312–327 | ENV 312–327 | ++ | +++ |
| | | Vac ENV | ++ | +++ |

[a] and [b]: of table II

TABLE V

Cytolytic activities found in 12 immunized macaques

| Macaque* | Effector cells[a] CD4/CD8 ratio[e] | Target cells[b] | % specific lysis[c] at E/T ratio[d] of: 70:1 | 23:1 | 7:1 | 2:1 |
|---|---|---|---|---|---|---|
| RS4 | 56/31 | HP | 8 | 7 | 2 | 0 |
|  |  | HP-GAG 165–195 (SEQ ID NO: 9) | 60[f] | 64 | 63 | 48 |
| RS7 | 4/78 | HP | 20 | 18 | 10 | 4 |
|  |  | HP-GAG 246–281 (SEQ ID NO: 10) | 59 | 41 | 25 | 12 |
| RS23 | 39/44 | HP | 18 | 10 | 4 | 1 |
|  |  | HP-NEF 201–225 | 42 | 29 | 8 | 2 |
| Q50 | 44/38 | — |  |  |  |  |
| Q51 | 48/39 | — |  |  |  |  |
| RS6 | 50/32 | HP | 11 | 11 | 9 | 6 |
|  |  | HP-NEF 155–178 (SEQ ID NO: 6) | 40 | 34 | 21 | 11 |
| Q53 | 27/56 | — |  |  |  |  |
| Q54 | 54/31 | — |  |  |  |  |
| RS17 | 21/72 | HP | 0 | 0 | 0 |  |
|  |  | HP-NEF 155–178 (SEQ ID NO: 6) | 44 | 43 | 28 |  |
| RS20 | 34/47 | HP | 5 | 5 | 0 |  |
|  |  | HP-NEF 125–147 (SEQ ID NO: 5) | 70 | 64 | 38 |  |
|  |  | HP-NEF 155–178 (SEQ ID NO: 6) | 53 | 42 | 20 |  |
| RS21 | 43/51 | HP | 23 | 20 | 18 |  |
|  |  | HP-NEF 201–225 (SEQ ID NO: 7) | 35 | 29 | 20 |  |
| RS22 | 36/50 | — |  |  |  |  |

Legends table V:
[a]PBMC were obtained from 12 immunized macaques and restimulated by the mixture of the 7 peptides in vitro.
[b]target cells were autologous B-LCL immortalized by the herpes papio virus and incubated with peptide (20 μM).
[c]target cells (5 · 10³) were labeled with ⁵¹Cr and incubated for 4 hours with various numbers of effector cells.
[d]E/T ratio, effector to target ratio.
[e]Phenotypes were performed on cell cultures just before the CRT.
[f]CRT was considered as positive if the specific chromium release observed against peptide-pulsed target cells exceeded that observed on B-LCL without peptide by more than 10% at the highest E:T ratio.

TABLE VI

CTL recognized autologous target cells infected with vaccinia virus

| Effector cells[a] Macaque* | Target cells[b] | % Specific lysis[c] at E/T ratio[d] of: 210:1 | 70:1 | 23:1 | 7:1 |
|---|---|---|---|---|---|
| RS4 | HP-VAC-WT | 22 | 14 | 11 | 2 |
|  | HP-VAC-GAG | 70[e] | 51 | 32 | 36 |
| RS6 | HP-VAC-WT | 16 | 2 | 0 | 0 |
|  | HP-VAC-NEF | 36 | 11 | 1 | 0 |
| RS7 | HP-VAC-WT | 34 | 22 | 23 | 21 |
|  | HP-VAC-GAG | 46 | 37 | 22 | 25 |
| RS23 | HP-VAC-WT | 43 | 16 | 17 | 8 |
|  | HP-VAC-NEF | 64 | 34 | 21 | 11 |
| RS17 | HP-VAC-WT |  | 10 | 3 | 5 |
|  | HP-VAC-NEF |  | 17 | 7 | 9 |
| RS20 | HP-VAC-WT | 11 | 3 | 8 | 4 |
|  | HP-VAC-NEF | 30 | 22 | 23 | 17 |
| RS21 | HP-VAC-WT | 22 | 22 | 27 | 8 |
|  | HP-VAC-NEF | 61 | 50 | 52 | 23 |

Legends Table VI:
[a]PBMC were obtained from 12 immunized macaques and restimulated by the mixture of the 7 peptides in vitro.
[b]target cells were autologous B-LCL immortalized by the herpes papio virus and infected with a wild type (WT) or Nef or Gag recombinant vaccinia virus.
[c]target cells (5 · 10³) were labeled with ⁵¹Cr and incubated for 4 hours with various numbers of effector cells.
[d]E/T ratio; effector to target ratio.
[e]CRT was considered as positive if the specific chromium release observed against target cells presenting SIV antigens exceeded that observed on targets infected with the wild type vaccinia virus by more than 10% for 210:1 E/T ratio or 5% for 70:1 E:T ratio.

TABLE VII

Fine specificities of CTL

| Peptides (amino acid position) | Specific cytolytic activity for monkey and E/T ratio[a] | | | | | | | |
|---|---|---|---|---|---|---|---|---|
|  | RS4 | | RS17 | | RS20 | | RS23 | |
|  | 60:1 | 20:1 | 60:1 | 20:1 | 60:1 | 20:1 | 60:1 | 20:1 |
| NEF 125–147 (SEQ ID NO: 5) |  |  |  |  | 72 | 76 |  |  |
| NEF 125–138 |  |  |  |  | 70 | 85 |  |  |
| NEF 133–147 |  |  |  |  | 0 | 4 |  |  |
| NEF 155–178 (SEQ ID NO: 6) |  |  | 44 | 43 | 74 | 87 |  |  |
| NEF 155–169 |  |  | 0 | 0 | 12 | 14 |  |  |
| NEF 160–176 |  |  | 0 | 0 | 0 | 6 |  |  |
| NEF 164–178 (SEQ ID NO: 11) |  |  | 42 | 46 | 47 | 49 |  |  |
| NEF 201–225 (SEQ ID NO: 7 |  |  |  |  |  |  | 23 | 14 |
| NEF 201–215 |  |  |  |  |  |  | 18 | 11 |
| NEF 211–225 |  |  |  |  |  |  | 0 | 0 |
| GAG 165–195 (SEQ ID NO: 9) | 52 | 57 |  |  |  |  |  |  |

TABLE VII-continued

Fine specificities of CTL

| | Specific cytolytic activity for monkey and E/T ratio[a] | | | | | | | |
|---|---|---|---|---|---|---|---|---|
| Peptides | RS4 | | RS17 | | RS20 | | RS23 | |
| (amino acid position) | 60:1 | 20:1 | 60:1 | 20:1 | 60:1 | 20:1 | 60:1 | 20:1 |
| GAG 165–185 | 9 | 8 | | | | | | |
| GAG 176–195 | 44 | 35 | | | | | | |

[a]The CRT was performed after 3 in vitro stimulations of PBMC from immunized macaques. Target cells were prepared from autologous B-LCL. The percent specific chromium release was measured for each target cell incubated with each peptide. The lysis of autologous B-LBL without peptide was always less than 5%. E/T ratio, effector to target ratio.

What we claim:

1. A lipopeptide comprising a peptide having between 10 and 40 amino acids and at least one antigenic determinant, said lipopeptide also comprising at least one chain derived from a member selected from the group consisting of pimelautide, trimexautide, hexadecanoic acid and 2-aminohexadecanoic acid and/or steroid groups coupled on the α-NH$_2$ and/or ε-NH$_2$ functional groups of said amino acids.

2. The lipopeptide of claim 1 wherein the steroid is N-lysine.

3. The lipopeptide of claim 1 wherein the steroid is (cholest-5-enyl-3-oxy)-acetic acid.

4. The lipopeptide of claim 1 wherein the peptide is a fragment of a protein of the HIV-1 or HIV-2 viruses.

5. The lipopeptide of claim 4 wherein the peptide fragment is a fragment of the proteins encoded by a gene selected from the group consisting of the ENV-gene, the NEF gene, and the GAG gene.

6. The lipopeptide of claim 5 wherein the fragment is of the protein encoded by the ENV-gene and is selected from the group of the 312–327 fragment, the 302–336 fragment and the 307–331 fragment.

7. The lipopeptide of claim 1 wherein the chain derived from hexadecanoic acid is N-palmitoyl lysine.

8. The lipopeptide of claim 1 wherein the chain derived from hexadecanoic is N-ε-palmitoyl lysine.

9. The lipopeptide of claim 1 wherein the chain derived from hexadecanoic acid N-ε-palmitoyl lysilamide.

* * * * *